(12) United States Patent
Evans et al.

(10) Patent No.: US 6,685,678 B2
(45) Date of Patent: Feb. 3, 2004

(54) DRUG DELIVERY AND MONITORING SYSTEM

(75) Inventors: Robert F. Evans, Mobile, AL (US); Michael F. Burrow, Lawrenceville, GA (US)

(73) Assignee: Docusys, Inc., Mobile, AL (US)

( * ) Notice: Subject to any disclaimer, the term of this patent is extended or adjusted under 35 U.S.C. 154(b) by 0 days.

(21) Appl. No.: 09/813,547

(22) Filed: Mar. 21, 2001

(65) Prior Publication Data

US 2001/0056258 A1 Dec. 27, 2001

Related U.S. Application Data

(60) Provisional application No. 60/191,155, filed on Mar. 22, 2000.

(51) Int. Cl.⁷ .................................................. A61M 5/00
(52) U.S. Cl. ........................ 604/207; 604/200; 604/208; 604/30; 604/28
(58) Field of Search ................................ 604/200, 207, 604/208, 206, 201, 65, 66, 67, 30, 31, 32, 33, 34, 28

(56) References Cited

U.S. PATENT DOCUMENTS

| | | | |
|---|---|---|---|
| 2,586,581 A | * 2/1952 | Tschischeck | .................... 88/39 |
| 3,045,494 A | * 7/1962 | Gerarde | ..................... 73/425.6 |
| 3,266,298 A | 8/1966 | Whitehead et al. | ............. 73/53 |
| 3,391,694 A | 7/1968 | Spaeth | ......................... 128/218 |
| 3,698,383 A | 10/1972 | Baucom | ..................... 128/2 G |
| 4,079,736 A | 3/1978 | Lundquist | ............... 128/214 R |
| 4,383,252 A | 5/1983 | Purcell et al. | .............. 340/606 |
| 4,559,044 A | 12/1985 | Robinson et al. | ............ 604/246 |
| 4,581,013 A | 4/1986 | Allen | ........................... 604/78 |
| 4,613,325 A | 9/1986 | Abrams | ........................ 604/65 |
| 4,853,521 A | * 8/1989 | Claeys et al. | ................ 235/375 |
| 4,976,687 A | 12/1990 | Martin | ......................... 604/65 |
| 5,391,081 A | 2/1995 | Lampotang et al. | ......... 434/262 |
| 5,401,253 A | * 3/1995 | Reynolds | ..................... 604/206 |
| 5,449,344 A | 9/1995 | Taylor et al. | .................. 604/97 |
| 5,449,345 A | 9/1995 | Taylor et al. | ................ 604/100 |
| 5,533,981 A | * 7/1996 | Mandro et al. | .............. 604/208 |
| 5,569,212 A | 10/1996 | Brown | ......................... 604/207 |
| 5,584,701 A | 12/1996 | Lampotang et al. | ......... 434/272 |
| 5,593,390 A | 1/1997 | Castellano et al. | .......... 604/187 |
| 5,628,309 A | 5/1997 | Brown | ......................... 128/632 |

(List continued on next page.)

FOREIGN PATENT DOCUMENTS

WO  WO 99/11306  3/1999

OTHER PUBLICATIONS

Alan F. Merry, Craig S. Webster, and Daniel J. Matthew, *A New, Safety–Oriented, Integrated Drug Administration and Automated Anesthesia Record System*, Society for Technology in Anestesia, 2001, pp. 385–390.

*Primary Examiner*—Ira S. Lazarus
*Assistant Examiner*—Tu Cam Nguyen
(74) *Attorney, Agent, or Firm*—Lerner, David, Littenberg, Krumholz & Mentlik, LLP

(57) ABSTRACT

A drug administration system includes a cradle attached about an intravenous injection port having a flange extending therefrom. The cradle supports first drug administration information in the nature of machine and human readable code, for example, barcode. A syringe including a needle includes a flange extending from the syringe. The syringe supports second drug administration information in machine and/or human readable form. A scanner module is constructed to slidably receive the flange of the cradle and syringe whereby the syringe needle is aligned with the intravenous injection port. The module may be provided with an electronic scanning system for identifying the first and second drug administration information, as well as determining the amount of the drug being administered from the syringe to the injection port by monitoring movement of the syringe plunger. The information and data may be stored within the module for uploading to a remote location.

87 Claims, 20 Drawing Sheets

U.S. PATENT DOCUMENTS

| | | | |
|---|---|---|---|
| 5,643,212 A * | 7/1997 | Coutre et al. | 604/131 |
| 5,645,534 A | 7/1997 | Chanoch | 604/189 |
| 5,651,775 A * | 7/1997 | Walker et al. | 604/207 |
| 5,690,618 A | 11/1997 | Smith et al. | 604/232 |
| 5,692,640 A | 12/1997 | Caulfield et al. | 221/70 |
| 5,697,916 A * | 12/1997 | Schraga | 604/201 |
| 5,704,922 A | 1/1998 | Brown | 604/207 |
| 5,716,345 A | 2/1998 | Halbich | 604/207 |
| 5,720,733 A | 2/1998 | Brown | 604/207 |
| 5,772,443 A | 6/1998 | Lampotang et al. | 434/272 |
| 5,782,814 A | 7/1998 | Brown et al. | 604/207 |
| 5,792,117 A | 8/1998 | Brown | 604/207 |
| 5,925,021 A | 7/1999 | Castellano et al. | 604/207 |
| 5,928,201 A * | 7/1999 | Poulsen et al. | 604/208 |
| 6,070,761 A * | 6/2000 | Bloom et al. | 222/81 |
| 6,485,465 B2 * | 11/2002 | Moberg et al. | 604/154 |

* cited by examiner

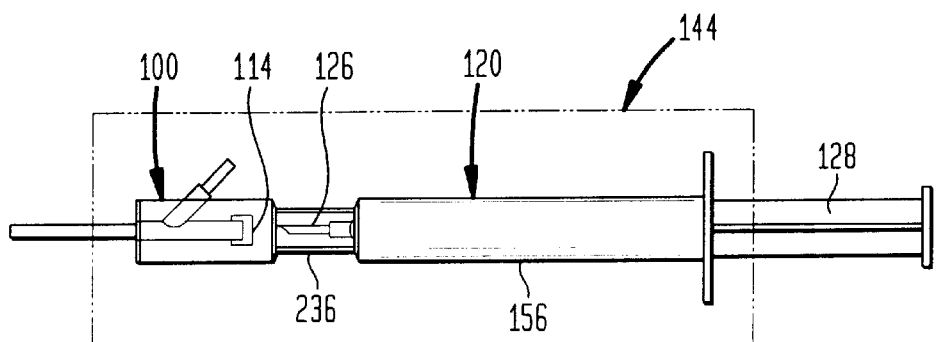
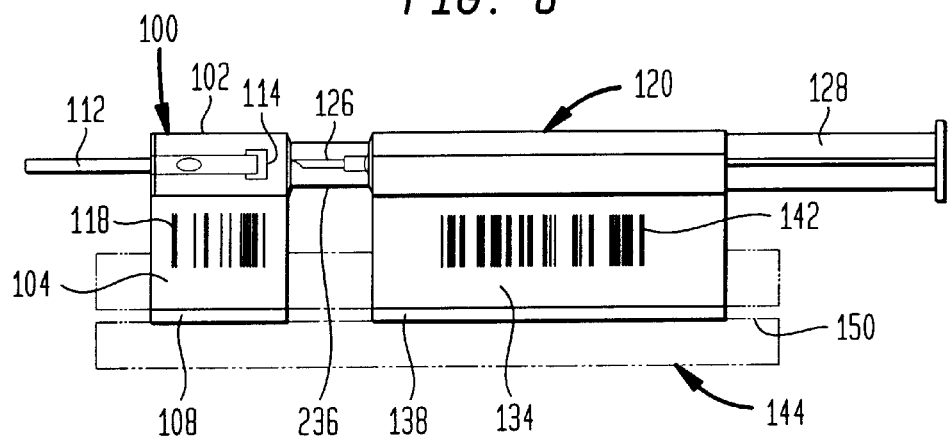
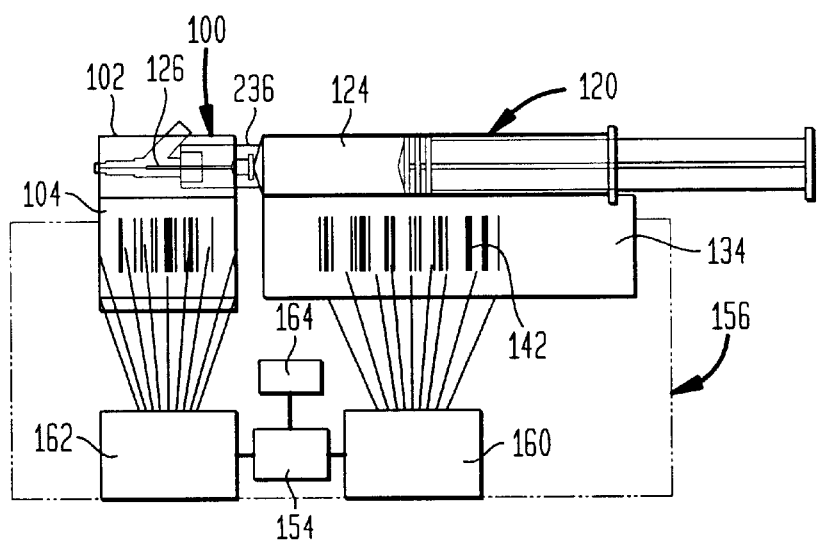

FIG. 17A
FIG. 17B
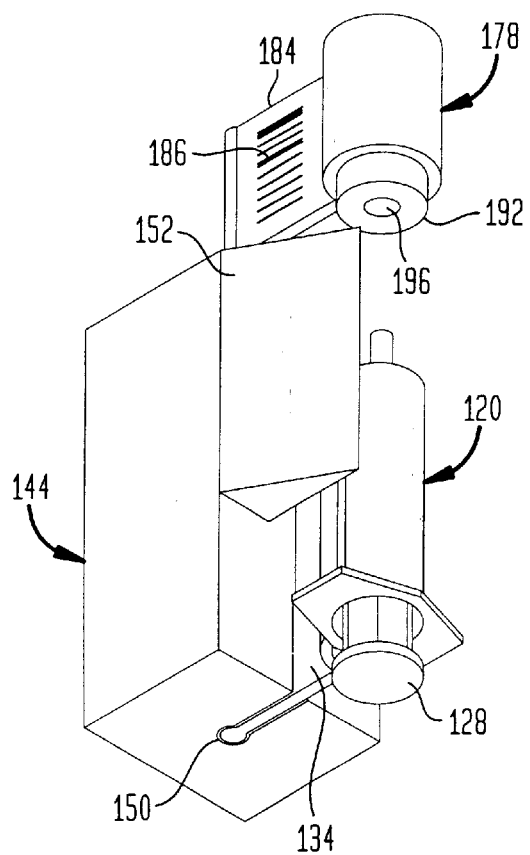
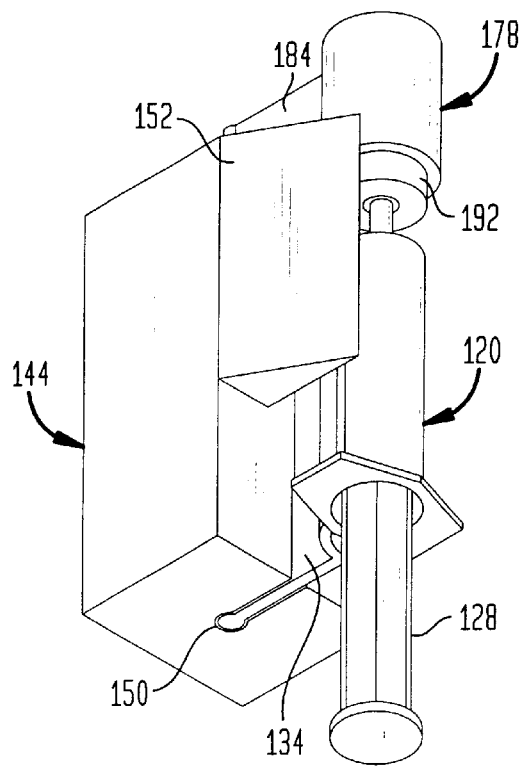

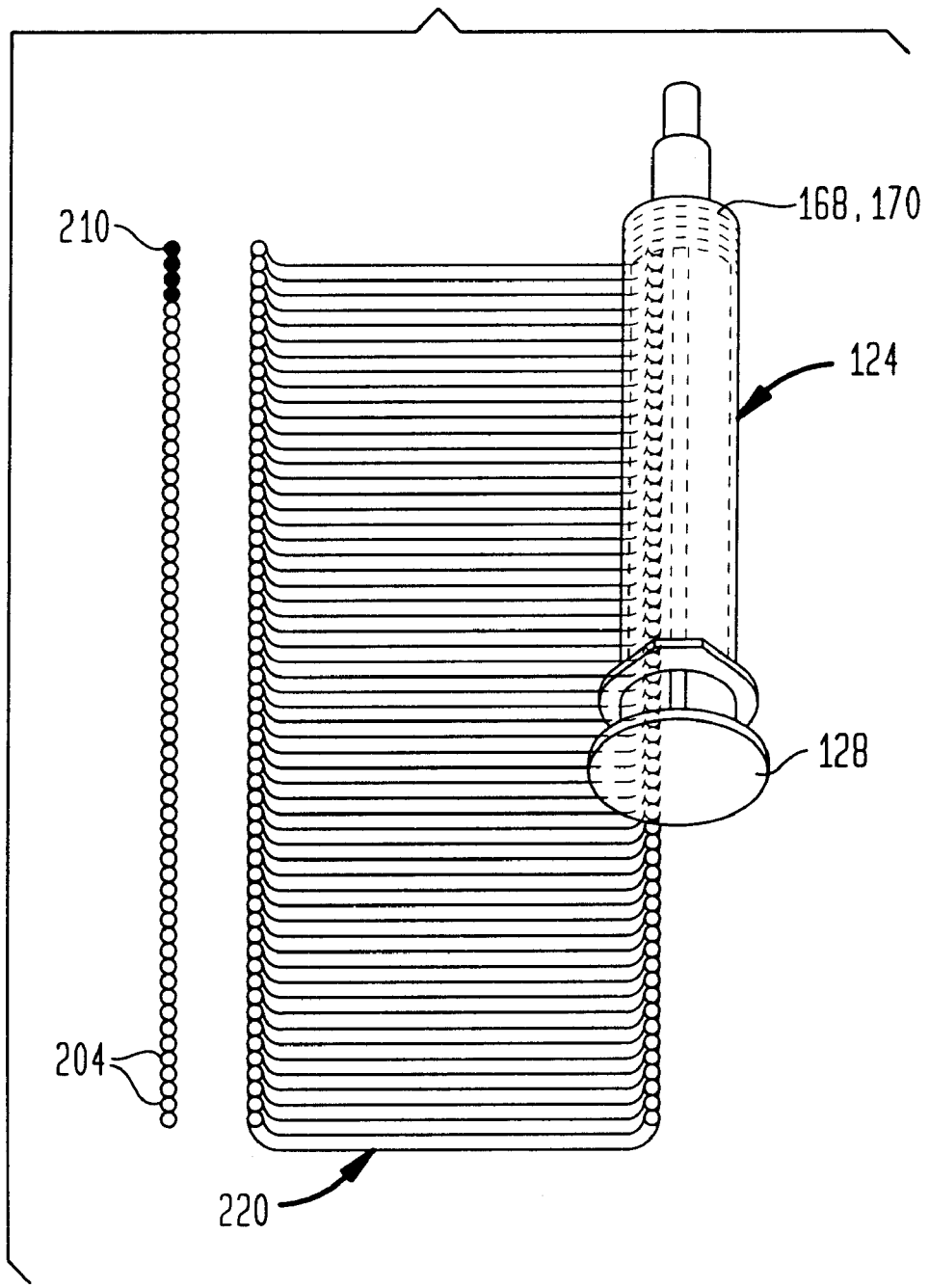

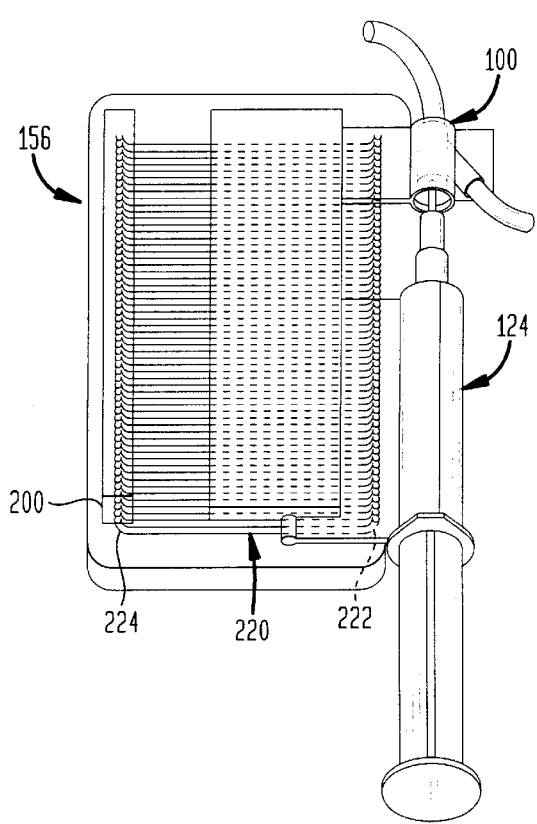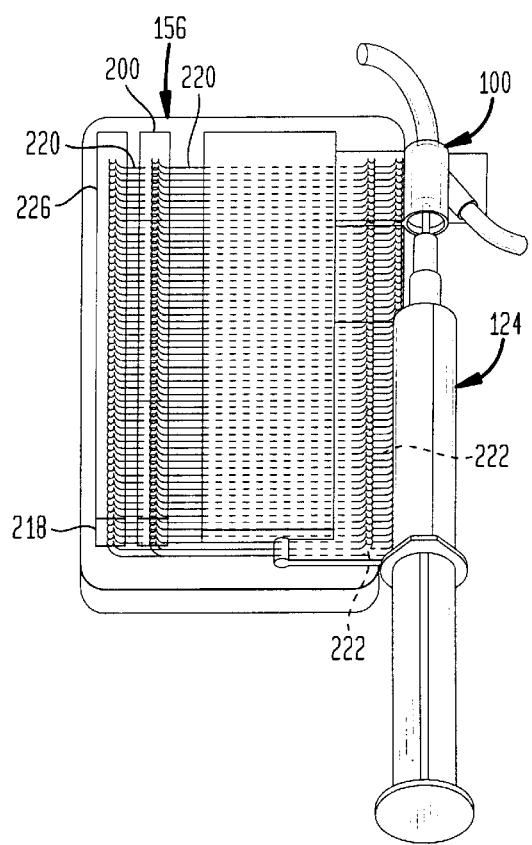

DRUG DELIVERY AND MONITORING SYSTEM

CROSS-REFERENCE TO RELATED APPLICATIONS

The present application claims the benefit of United States Provisional Application No. 60/191,155, filed Mar. 22, 2000, the disclosure of which is hereby incorporated by reference herein.

BACKGROUND OF THE INVENTION

The present invention relates in general to the field of drug delivery, and more particularly, to drug delivery and monitoring systems having drug administration information and data storage capability.

An alarming number of adverse drug events occur nationally contributing significantly to morbidity and mortality, as well as immense expense. Major contributing factors include the necessity of health care workers to perfectly identify, prepare and administer medications after properly identifying the patient and remembering allergies, drug—drug interactions, the patient medical conditions and then recalling drugs and dosing for charting on the patient's record.

A number of systems are known for monitoring drug delivery to a patient through an IV injection port. For example, see Martin, U.S. Pat. No. 4,976,687; Abrams, U.S. Pat. No. 4,613,325; Robinson, et al., U.S. Pat. No. 4,559,044; Purcell, et al.; U.S. Pat. No. 4,383,252; and Lundquist, U.S. Pat. No. 4,079,736.

A drug documenting system has been disclosed using optical scanning techniques in Walker, et al., U.S. Pat. No. 5,651,775, the disclosure of which is incorporated herein in its entirety by reference. In Walker, et al., a scanner module includes a reader for entering and storing drug administration information and data on a magnetic card by operation of a microprocessor. The scanner module includes one or more photo sensing electronic detectors for reading machine readable drug administration information provided on a label adhered to a syringe and determining drug volume delivery data in real time. A PCMCIA slot provides system communication through the use of a modem or connection to an area network. The scanner module may be integrated into a system at a fixed location or rendered portable by battery power. By reducing the sensing system size and connecting to wireless communicating devices, added safety and utility can be made available to patients. Notwithstanding the foregoing, there remains the desire for improvements in drug delivery and monitoring systems, which are fulfilled by the system of the present invention.

SUMMARY OF THE INVENTION

The present invention relates to detecting and documenting drug delivery events using a scanner module for patients receiving injectable medications. By digitizing this information, a log of which patient received what medication and how much, can be transferred to a computerized patient record for temporary or permanent storage. Furthermore, when designed as part of a data network, the drug about to be given to a patient can be checked against the patient's database of other medications, allergies and health conditions allowing warning to the health care professional of possible adverse drug events like administering a drug for which the patient is known to be allergic. Thus, the scanner module can be portable, handheld and have wireless data transceiving capabilities, as well as on-board memory and a microcomputer, allowing the module to function as a point-of-care medication delivery documentation device.

In accordance with various aspects of the present invention, an intravenous injection port cradle is provided with a patient identifying bar or similar machine and/or human readable code permanently affixed to the cradle. The injection port cradle can be used not only for aligning with the syringe using a scanner module for intravenous drug administration, but can carry a patient identifier, e.g., bar code, that will be read by the system in conjunction with the syringe which is mounted to a syringe label cradle. This provides the ability to verify that the right drug matches the correct patient, and affords benefits when the patient is moved or transferred in hospital (i.e., radiology, X-ray, etc.). In this regard, the port cradle and patient identifying information goes with the patient throughout their hospital stay. The barcode can either be one dimension barcode or two dimension, which provides more data on the barcode including a patient photo if desired.

A drug container or ampule similarly attached to a drug cradle is designed to cause a syringe similarly mounted to a scanner module to automatically align therewith. The drug cradle also has an area which holds a unique identifying code for the drug which is machine readable. The handheld scanner module can hold the syringe label cradle, drug cradle and/or the patient intravenous port cradle. The scanner module causes the syringe to automatically align with either the patient injection port or the drug supply container. This alignment facilitates the filling of syringes with the medication and subsequent use by the clinician. When the medication container in its cradle is removed from the scanner module, an injection port carried in the port cradle may be advanced into the scanner module and be caused to automatically align with the filled syringe. Depression of the plunger of the syringe causes the medication to be dispensed into the intravenous tubing connected to a patient's vein.

The port cradle is held away from contamination and in a manner which allows easy and accurate alignment with syringes full of medications similarly mounted on matching cradles. The two cradle systems cause alignment of the needle of the syringe with the orifice or center septum of medication supply containers. A syringe filled in this manner and remaining attached to the scanner module can then be dispensed into the IV port which also mounts onto the scanner module. The scanner module allows in-field preparation and use of medications directly from the supply container into the syringe, and then into the patient without removing the syringe from the module. This allows for the digital documentation of the conjoining of these labels and their drug administration information, as well as the movement of the syringe plunger. By temporarily storing this information or by immediately transmitting this information, the medication delivery event can be communicated to an automatic clinical record or hospital information system. By securing the medication supply vials or ampules in the drug cradle, the medications can be organized for storage or deployment in the clinical setting. These drug cradles help mount the medications in a transport tray for easy identification and accounting.

The scanner module according to one aspect of the invention is in the nature of a syringe mounting and sensing device which (1) causes automatic alignment of the needle of the syringe with an injection port of an intravenous tubing connected to a catheter delivering solutions to a patient or (2) directly to the patient by intramuscular or (3) subcutaneous injection routes. The scanner module in one embodiment uses an array of fiber optic conductors to route an image of the syringe plunger to a detector which senses light levels reflecting the position of the dark syringe plunger seal. The position of the plunger thereby sensed is converted into a digital report of the movement of the syringe plunger and when coupled with information about the size of the syringe, the drug in the syringe and concentration, the amount of medication delivered to the patient may be encoded. A second fiber optic array can be used to read information encoded into a barcode on the label portion of the syringe cradle. The drug information and plunger position are transferred to an attached handheld computing device for storage and ultimate uploading to patient information systems. The identity of the patient receiving the medication may likewise be sensed by a barcode attached to the intravenous delivery port cradle or by scanning the patient's identification via a barcode such as a wristband or similar tag.

Fiber optic channels are known to conduct light around curves and may be used to illuminate or transmit areas of light and dark. By closely aligning a linear array of fiber optic channels to the barrel of the syringe and then routing the fiber optic channels to a linear CCD (charged coupled device or similar photosensing electronic detector) the position of the plunger can be determined by polling the light level incident upon the discrete components of the photosensor's array. When a fiber optic array is similarly aligned with a patient identifying barcode and a drug identifying barcode, the entire drug event may be actively monitored and alerts can be given to a clinician warning against adverse drug errors.

In accordance with one embodiment of the present invention there is described a drug delivery and monitoring system comprising a scanner module including a first and second detector module, the first detector module determining drug administration data and identifying first drug administration information, the second detector module identifying second drug administration information, the scanner module including a storage device for storing the data and the first and second information; a syringe including a barrel and a plunger moveable therein for administration of a drug, the syringe having the first drug administration information provided in association therewith, the syringe constructed to be releasably attached to the scanner module in operative association with the first detector module, whereby movement of the syringe relative to the first detector module causes the first detector module to identify the first drug administration information for storage in the storage device and movement of the plunger within the barrel causes the first detector module to determine the drug administration data for storage in the storage device; a port cradle attachable to an injection port, the cradle having the second drug administration information provided in association therewith, the cradle constructed to be releasably attached to the scanner module in operative association with the second detector module, whereby movement of the cradle relative to the second detector module causes the second detector module to identify the second drug administration information for storage in the storage device.

In accordance with another embodiment of the present invention there is described a drug delivery and monitoring system comprising a scanner module including a first and second detector module, the first detector module determining drug administration data and identifying first drug administration information, the second detector module identifying second drug administration information, the scanner module including a storage device for storing the data and the first and second information; a syringe including a barrel having a flange extending therefrom and a plunger moveable therein for administration of a drug, the syringe having the first drug administration information provided on the flange, the scanner module constructed to slidingly receive the flange of the syringe in operative association with the first detector module, whereby movement of the syringe relative to the first detector module causes the first detector module to identify the first drug administration information for storage in the storage device and movement of the plunger within the barrel causes the first detector module to determine the drug administration data for storage in the storage device; a port cradle having a flange extending therefrom attachable to an injection port, the cradle having the second drug administration information provided on the flange thereof, the scanner module constructed to slidingly receive the flange of the cradle in operative association with the second detector module, whereby movement of the cradle relative to the second detector module causes the second detector module to identify the second drug administration information for storage in the storage device; a microprocessor in operative association with the first and second detector modules and the storage device.

In accordance with another embodiment of the present invention there is described a cradle for attachment to a drug container, the cradle comprising a housing for attachment about a drug container, and a flange extending therefrom, the flange supporting thereon drug administration information.

In accordance with another embodiment of the present invention there is described a cradle for attachment to an injection port, the cradle comprising a housing for attachment about an injection port, and a flange extending therefrom, the flange supporting thereon drug administration information.

In accordance with another embodiment of the present invention there is described a method for monitoring drug delivery to an injection port, the method comprising positioning a scanner module adjacent an injection port, the scanner module including first and second detector modules, the first detector module determining drug administration data and identifying first drug administration information, the second detector module identifying second drug administration information, the scanner module including a storage device for storing the data and the first and second information; releasably securing a syringe loaded with a drug to be administered to the scanner module, the syringe having the first drug administration information provided in association therewith, identifying the first drug administration information by the first detector module, releasably securing a port cradle attached to an injection port to the scanner module, the port cradle having the second drug administration information provided in association therewith, identifying the second drug administration information by the second module detector, determining the drug administration data by the first detector module regarding the drug being delivered from the syringe to the injection port, and storing in the scanner module the first and second drug administration information and the drug administration data.

In accordance with another embodiment of the present invention there is described a method for monitoring drug delivery to an injection port, the method comprising positioning a scanner module adjacent an injection port in fluid communication with a patient, the scanner module including first and second detector modules, the first detector module determining drug administration data and identifying first drug administration information, the second detector module identifying second drug administration information, the scanner module including a storage device for storing the data and the first and second information; releasably securing a syringe loaded with a drug to be administered to the scanner module, the syringe including a flange having the first drug administration information provided thereon, moving the flange of the syringe into operative association with the first detector module, identifying the first drug administration information by the first detector module, releasably securing a port cradle attached to an injection port to the scanner module, the port cradle including a flange having the second drug administration information provided thereon, making the flange of the port cradle into operative association with the second detector module, identifying the second drug administration information by the second detector module, determining the drug administration data by the first detector module regarding the drug being delivered from the syringe to the injection port, wherein the syringe includes a plunger for delivering the drug therefrom and wherein the determining the drug administration data comprises determining the distance of movement of the plunger within the syringe during drug delivery and storing in the scanner module the first and second drug administration information and the drug administration data.

In accordance with another embodiment of the present invention there is described a method for delivering and monitoring drugs to an injection port connected to a patient, the method comprising delivering a needle on a drug loaded syringe to the injection port, automatically determining identification information relative to the drug contained in the syringe by electronically scanning a label associated with the syringe, automatically determining information relative to the patient by electronically scanning a label associated with the injection port, pushing a plunger of the syringe to deliver a quantity of the drug through the port, monitoring movement of the plunger while delivering the drug for determining the volume of the drug delivered from the syringe, and storing the patient information obtained by scanning the label and the quantity of the drug delivered from the syringe.

In accordance with another embodiment of the present invention there is described a method for delivering and monitoring drugs to an injection port connected to a patient, the method comprising delivering a needle on a drug loaded syringe into the port, automatically determining identification information relative to the drug contained in the syringe by electronically scanning a label, pushing a plunger of the syringe to deliver a volume of the drug through the port, automatically determining information relative to the patient by electronically scanning a label associated with the injection port, monitoring movement of the plunger for the purpose of calculating the amount of drug delivered, and storing the patient information and amount of the drug delivered.

In accordance with another embodiment of the present invention there is described a method of determining patient information before administering a drug from a syringe to an injection port connected to the patient, the method comprising providing the patient information in machine readable form on a cradle for the injection port, and scanning the label by an electronic detector for reading the patient information before administering the drug.

In accordance with another embodiment of the present invention there is described a method of filling a syringe comprising providing a drug container cradle attached to a drug container, the drug container cradle having a flange extending therefrom supporting drug administration information, providing a scanner module having a detector for detecting the drug administration information, supporting a syringe having a needle by the scanner module, supporting the drug container cradle by the flange on the scanner module with the needle in alignment with the drug container, reading the drug administration information from the flange by the detector, inserting the needle into the drug container for loading the syringe, and storing the drug administration data within the scanner module.

In accordance with another embodiment of the present invention there is described a drug administration system comprising a cradle attached about an injection port having a flange extending therefrom, the cradle supporting first drug information, a syringe including a needle having a flange extending from the syringe, the syringe supporting second drug administration information, and a housing slidably receiving the flange of the cradle and the syringe, whereby the needle is aligned with the injection port.

BRIEF DESCRIPTION OF THE DRAWINGS

The above description, as well as further objects, features and advantages of the present invention will be more fully understood with reference to the following detailed description of a drug delivery and monitoring system, when taken in conjunction with the accompanying drawings, wherein:

FIG. 5 is a top plan view of a drug loaded syringed label cradle unit and port cradle having alignment of the syringe needle with the septum of the injection port when co-joined with the scanner module;

FIG. 6 is a front elevational view of a drug loaded syringed label cradle unit and port cradle having alignment of the syringe needle with the septum of the injection port when co-joined with the scanner module;

FIG. 8 is a diagrammatical illustration showing a scanner module having a pair of detector modules respectively dedicated to one of the machine readable bar or similar codes on the port cradle and syringe label cradle unit;

FIGS. 17A–17B are sequential views showing loading of the drug cradle containing a drug vial into the scanner module containing a syringe label cradle unit for filling the syringe with the contained drug;

FIGS. 27A–27B are sequential views showing a signal at the output end of the fiber optic bundle by detected movement of the plunger through the syringe from one end to the other;

FIG. 28 discloses a CCD array aligned with the output end of the fiber optic bundle having its input end arranged in alignment with the machine readable bar code on the port cradle and syringe label cradle unit;

FIG. 29 is a perspective view showing the assembly of FIG. 28 further including a second CCD device arranged at the output end of a second fiber optic bundle having its input end arranged in alignment with the barrel and plunger of the syringe;

DETAILED DESCRIPTION

Figure 1A:
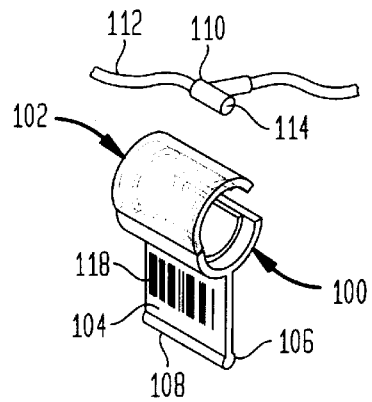
FIGS. 1A–1D are sequential illustrations showing the loading of an intravenous injection port, with supply tubing attached, into a port cradle, and optionally inserting a protective cap over the port cradle opening.
Figure 1B:
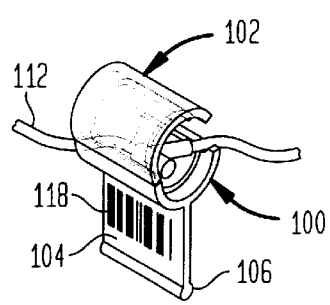
Figure 1C:
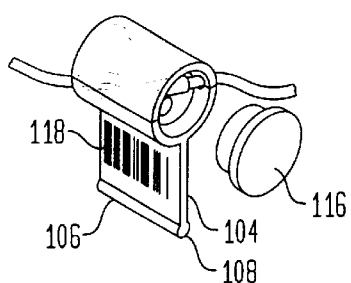
Figure 1D:
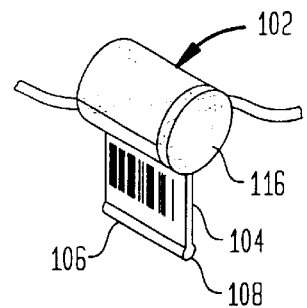

In describing the preferred embodiments of the present invention, specific terminology will be resorted to for the sake of clarity. However, the invention is not intended to be limited to the specific terms so selected, and is to be understood that each specific term includes all technical equivalence which operate in a similar manner to accomplish a similar purpose.

Referring now to the drawings, wherein like reference numeral represent like elements, there is shown in FIGS. 1A–1D a port cradle generally designated by reference numeral 100. The port cradle 100 includes a housing 102 from which there extends a planar flange 104 having a terminal end 106. The flange 104 may be integrally formed with the housing 102, extending outwardly therefrom. The flange 104 is substantially planar and generally coextensive with the length of the housing 102. However, it is to be understood that the flange 104 may be shorter or longer than that illustrated with respect to the length of the housing 102. The terminal end 106 may be formed in the nature of an elongated slider member 108 of generally uniform cross-section throughout its length, and as illustrated, a circular cross-section in accordance with one embodiment. As to be described hereinafter, the slider member 108 is operative for interlocking the port cradle 102 within a scanner module. As such, the slider member 108 may have various cross-sectional shapes, for example, oval, square, polygonal, irregular, etc. so as to mate with a corresponding elongated opening in the scanner module.

The housing 102 may be formed from a single tubular body of hollow or partially hollow construction, as well as from multiple parts which may be assembled together in forming the housing. To this end, the housing 102 may be formed from upper and lower housing halves which may be assembled together such as by snap-fit, hinge and locking mechanism, etc. In this regard, the housing 102 is intended to support an intravenous injection port 110 therein from which there extends flexible tubing 112 for intravenous drug injection to a patient. The housing 102 may interiorally include ribs or other conforming structure so as to securely hold the injection port 110 with its septum 114 centrally exposed at one end of the housing 102. It is also contemplated that the port cradle 100 and injection port 110 may be pre-fabricated into an integral unit for patient use. On the other hand, a technician may assemble the port cradle 100 to the injection port 110 at the patient's bedside. The open end of the housing 102 overlying the injection port 110 may be temporarily covered with a protective cap 116. The cap 116 will protect access to the septum 114 until removed prior to insertion of a needle from a syringe for drug administration.

Drug administration information 118 is preferably provided on the flange 104 in the form of a pre-printed label having an adhesive back. However, the drug administration information 118 may also be applied to the housing 102 if so desired. Also, the drug administration information 118 may be printed directly onto the flange 104 or housing 102. The drug administration information 118 includes a significant amount of man and/or machine readable information, and preferably, provides information on the drug name and drug concentration for easy viewing by an operator and/or barcode reader. Also, detailed drug information may include concentration, preparer, expiration date, expected size of syringe to be used, patient allergies, patient's current medication status, and other important drug delivery information may be contained within the drug administration information. Still further, the drug administration information 118 may include information regarding hospital billing information, patient information such as social security number and the like.

Figure 2A:
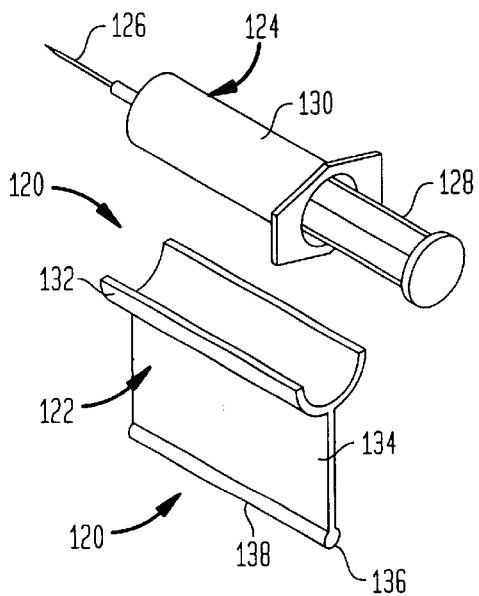
FIGS. 2A–2B are sequential views of preparing a syringe label cradle unit by loading a standard syringe onto a cradle and subsequently adhering same by application of a label containing machine readable bar or similar code.
Figure 2B:
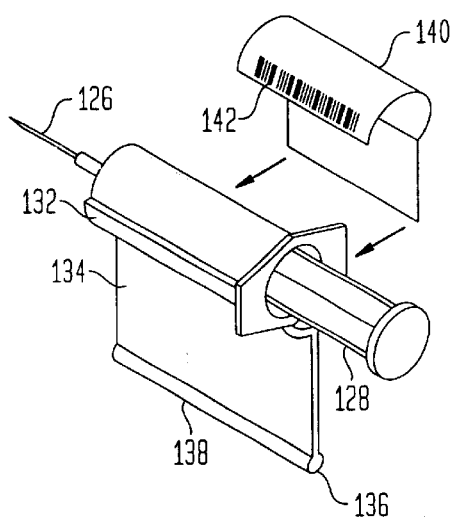

Referring now to FIGS. 2A–2B, there is illustrated a syringe label cradle unit (SLCU) 120. The SLCU 120 includes a syringe label cradle (SLC) 122 and a syringe 124 having a needle 126 and a plunger 128 which slides within syringe barrel 130. The SLC 122 includes a syringe support 132 and a planar flange 134 extending therefrom to a terminal end 136 constructed to include a slider member 138.

The syringe 124 may be attached to the SLC 122 such as by use of an adhesive, and preferably, by use of a label 140. As shown in FIG. 2B, the syringe barrel 130 is supported within the syringe support 132. A label 140 is thereafter adhered about the exposed portions of the syringe 124 and onto the planar opposed surfaces of the flange 134. The slider member 138 will be of similar construction to slider member 108 as described with respect to the port cradle 100. In this regard, the slider member 138 will also function to interlock the SLCU with a scanner module as to be described hereinafter. The SLCU, as thus far described, is constructed in a manner as disclosed in U.S. Pat. No. 5,651,775, the disclosure of which is incorporated herein by reference.

In another embodiment, the SLCU may be constructed as an integral member. In this regard, the syringe 124 may be provided with an integral depending flange 134 as described in co-pending U.S. patent application Ser. No. 09/454,184 entitled "Syringe For Use in a Drug Delivery System" filed on Dec. 3, 1999, the disclosure of which is incorporated herein by reference. The label 140, flange 134 or syringe barrel 130 may support drug administration information 142 of the type as thus far described with respect to drug administration information 118. In addition, any information considered pertinent to the patient and/or drug administration may be provided as part of the drug administration information 118, 142 which may be provided either in machine readable form or human readable form, or both.

Figure 3A:
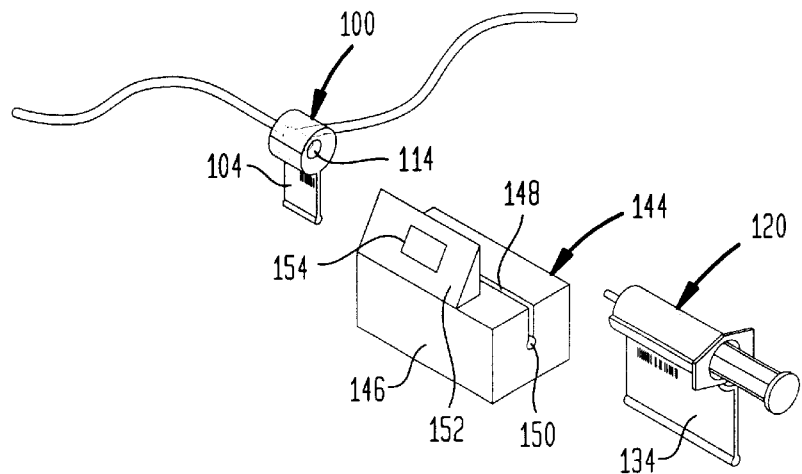
FIGS. 3A–3B are sequential views showing the sequence of co-joining the port cradle and the syringe label cradle unit into a slotted opening of a scanner module.
Figure 3B:
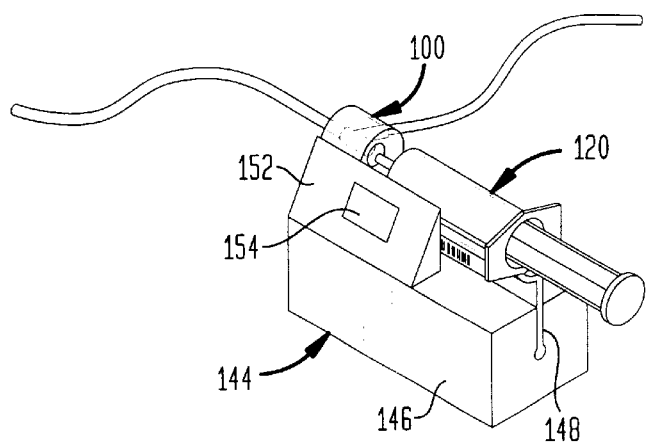
Figure 4:
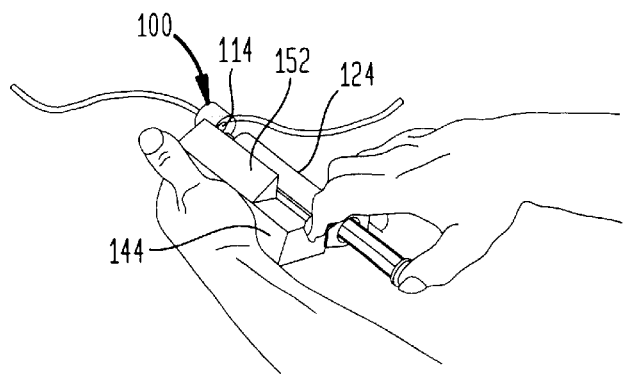
FIG. 4 is a perspective view showing use of the scanner module with co-joined port cradle and syringe label cradle unit.

Referring to FIGS. 3A–3B, there is illustrated a scanner module 144 constructed from a mounting rail 146 having an elongated slot 148 terminating at an elongated opening 150 configured of similar shape to slider members 108, 138 for capturing same. The scanner module 144 further includes a detector module 152 supported on the mounting rail 146 adjacent slot 148.

The detector module 152 performs a number of functions. The detector module 152 functions to read the drug administration information 118, 142 provided in association with the port cradle 100 and SLCU 120. In addition, the detector module 152 is operative for determining, in real time, the amount of the drug being administered by the syringe 124. In this regard, the detector module 152 will detect displacement of the plunger 128 for calculating via an integrated microprocessor drug administration data such as the volume of drug administered to the patient. The detector module 152 may include one or more detectors in the nature of a photosensing electronic device such as a charge coupled device (CCD) arranged in a matrix of sensing elements such as a linear or other array. The reading of the drug administration information 118, 142 and determining the amount of drug being administered, e.g., drug administration data, is performed in the manner as disclosed in U.S. Pat. No. 5,651,775. In general, the detector module 152 includes emitter-detector pair devices which are suitable for use in reading machine readable code such as barcodes, as well as detecting movement of an object such as the plunger 128.

As shown in FIGS. 3A–3B, the flange 104 of the port cradle 100 and flange 134 of the SLCU 120 are inserted into the slot 148 within the scanner module 144. The respective slider members 108, 138 are captured within the opening 150 so as to retain the port cradle 100 and SLCU 120. The drug administration information 118, 142 are read from the port cradle 100 and SLCU 120 by the detector module 152. This information may be stored in situ within a storage device which is controlled by an on board microprocessor 154.

Figure 7:
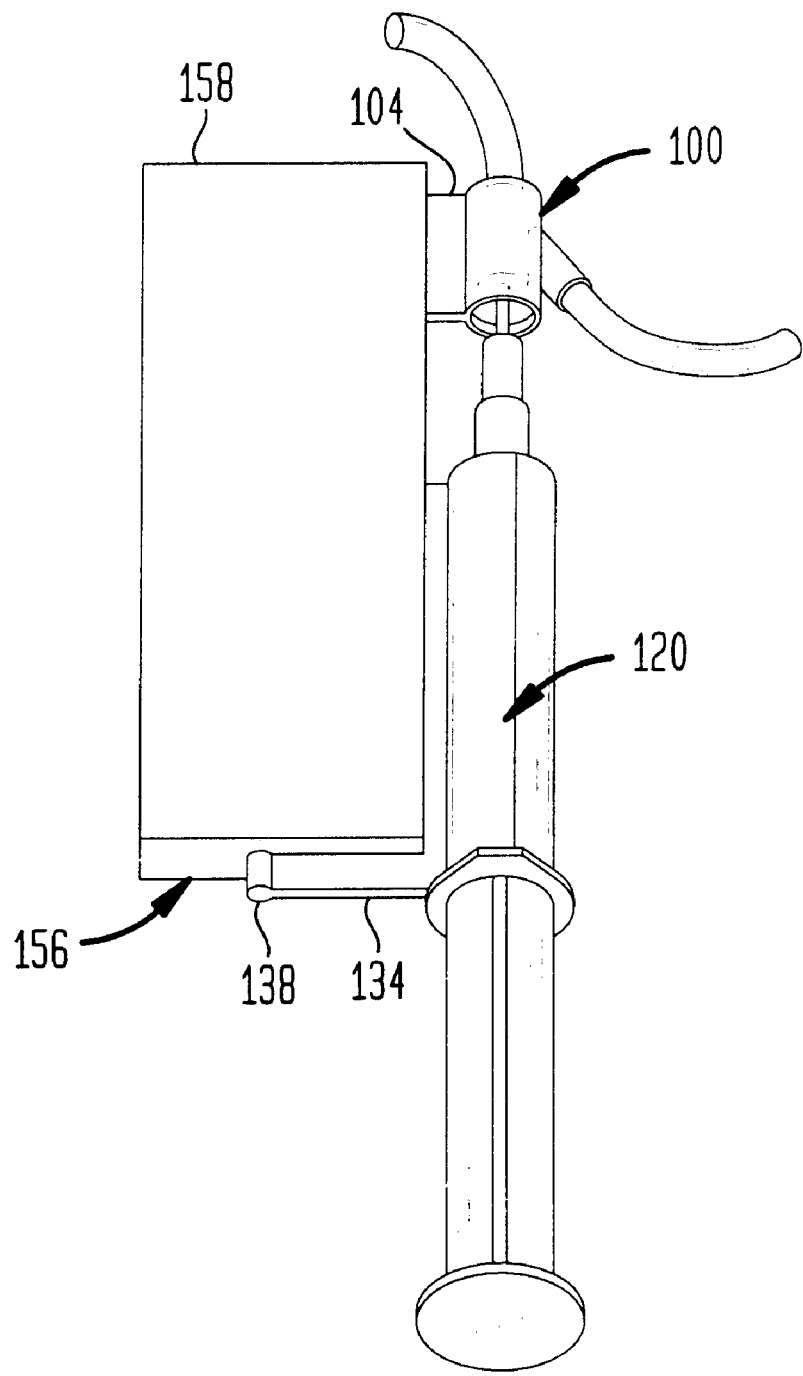
FIG. 7 is a perspective view showing the port cradle and syringe label cradle unit co-joined with a variation of a scanner module.

As shown in FIGS. 5–6, the needle 126 of the syringe 124 is aligned with and inserted into the septum 114 of the injection port 110 while being held by the scanner module 144. As the plunger 128 is depressed, its displacement is determined by the detector module 152 for computing the drug administration data, e.g., volume of drug administered in real time. This data is stored by the microprocessor 154. A further detailed explanation for determining the amount of drug being administered in real time is disclosed in U.S. Pat. No. 5,651,775. Although the detector module 152 is shown attached to the mounting rail 146, it is to be understood that the detector module may be incorporated into the body of the mounting rail as shown in FIG. 7. In this regard, the drug administration information 118, 142 will be aligned within the slot 148 as opposed to extending thereabove as shown in FIG. 3B. As such, the internal detector module 152 will read the drug administration information 118, 142 in a similar manner.

As previously noted, the needle 126 is aligned with the septum 114 of the injection port 110 as shown in FIG. 6. Syringes 124 come in a variety of sizes, for example, 20 ml, 10 ml, 5 ml, 3 ml and 1 ml. By varying the height of the flanges 104, 134 of the respective port cradle 100 and SLC 122, the needle 126 may be collinear aligned with the injection port 110 by accommodating the changing diameter of the barrel 130 of the syringe 124. For example, as the barrel diameter of the syringe 124 decreases for smaller syringes, the width of the flanges 104, 134 will increase to maintain alignment. The variable width of the flanges 104, 134 is accommodated by location of the opening 150 in the mounting rail 146.

Referring to FIG. 7, there is shown an integrated version of a scanner module generally designated by reference numeral 156. In this regard, the detecting devices are incorporated into the housing 158 to provide a compact unit enhancing the portability of the scanner module 156 from site to site of drug administration. Portability of the scanner module 156 can be enhanced using battery power and low power CMOS components, as well as miniature detector devices and fiber optics as to be described hereinafter.

Referring to FIG. 8, there is shown the incorporation of two detectors 160, 162 within the housing 158 of the scanner module 156. Detector 160, such as a linear CCD digital optical device is aligned for reading the drug administration information 142 on the syringe 124. Detector 162, similarly a CCD optical device is operative for reading the drug administration information 118 on the port cradle 100. The drug administration information 118, 142 can be stored in a storage device 164 controlled by microprocessor 154. The storage device 164 may be constructed in a variety of forms, for example, a semiconductor memory chip such as a RAM or insertable magnetic card. The drug administration information 118 from the port cradle 100 can be compared with the drug administration information 142 from the syringe 124. In the event of a mismatch of such information, for example, patient's identification, the technician can be alerted through either a visible or audible signal to prevent drug administration. Other conflicts might result from the wrong drugs and/or amounts, drug interactions and the like. It is also contemplated that the detectors 160, 162 can be integrated into a single detector which will function to scan and read the drug administration information 118, 142 from each of the port cradle 100 and SLCU 120. In the preferred embodiment, the detectors 160, 162 are in the nature of linear barcode scanners or a raster scanner operative for reading bar or other machine readable code for providing drug administration information.

Figure 9:
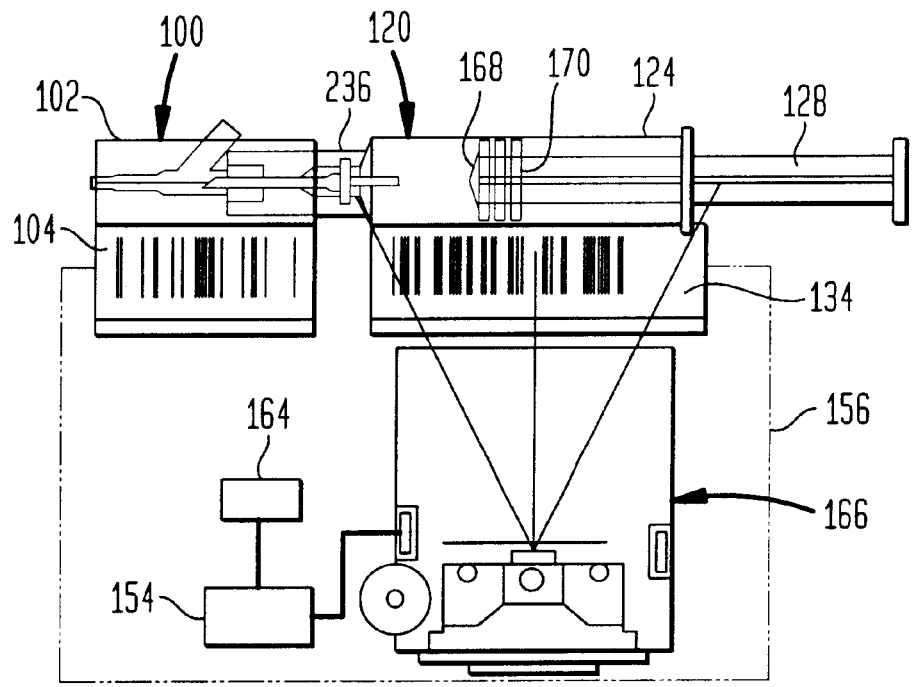
FIG. 9 is a diagrammatic illustration showing a detector module within the scanner module for detecting the syringe barrel and plunger movement therein.
Figure 10:
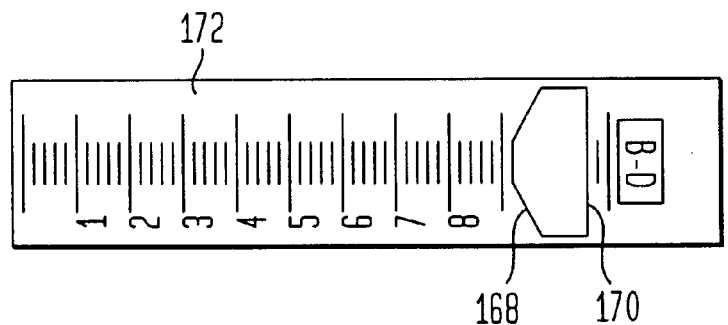
FIG. 10 is a diagrammatic image generated by the detector module shown in FIG. 9.

Referring to FIG. 9, there is further disclosed a detector 166, for example a CCD digital optical device, which is focused onto the syringe barrel 130. The detector 166 functions to determine movement of the plunger 128 for calculating the amount or volume of drug being administered in real time. The end of the plunger 128 supports a plunger tip seal 168. An optical signature of the syringe 124 is detected by the detector 166 as shown in FIG. 10. The duplicate image of the syringe barrel 130 is used for pattern recognition by pattern recognition software stored in the microprocessor 154. In this regard, the edge 170 of the plunger tip seal 168 is determined by the detector 166. A surveillance window 172 is controlled by the microprocessor software to enable scanning of the window for identification of the location of the plunger tip seal 168 during the process of drug administration. In this regard, the detector 166 in the nature of a digital optical device is calibrated to find and locate the black plunger tip seal 168 in a background of white within the surveillance window 172. By determining the distance of movement of edge 170 during drug administration, the microprocessor 154 can determine the amount of drug being administered to the patient in the nature of drug administration data. The drug administration data may be stored in the storage device 164 by operation of the microprocessor 154. In the preferred embodiment, the detector 162 is in the nature of a two-dimensional image or laser optical scanner.

Figure 11:
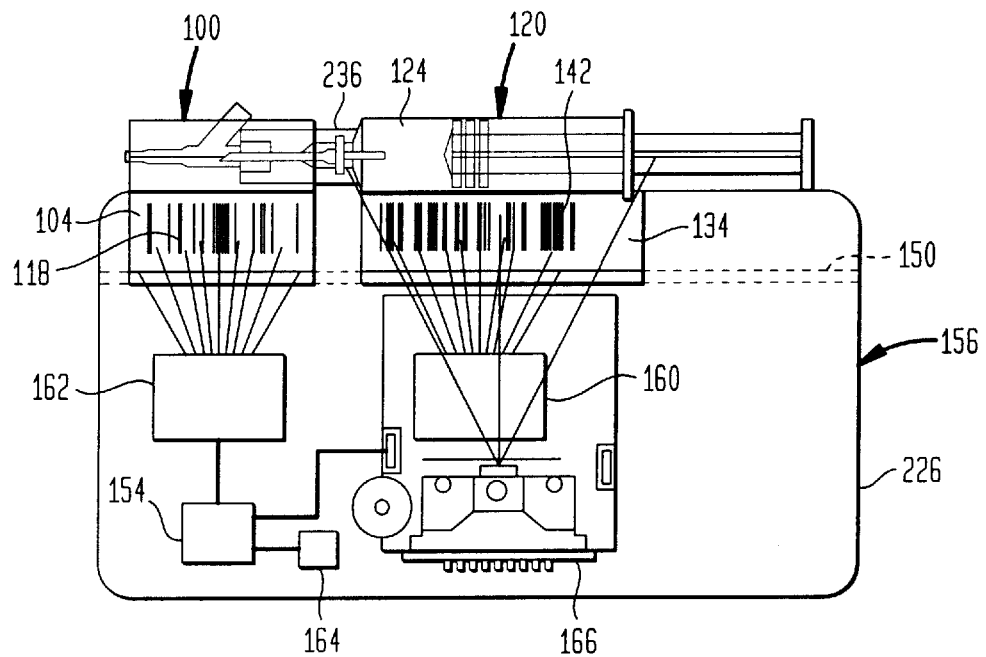
FIG. 11 is a diagrammatic illustration of the scanner module showing the operative relationship of the detectors for reading the bar or similar code on the port cradle and syringe label cradle unit and plunger movement during drug administration.

Referring to FIG. 11, there is diagrammatically shown the scanner module 156 in fully assembled form including detectors 160, 162, 166, microprocessor 154 and storage device 164. As shown, the components of the scanner module 156 are all internal within the housing, as well as the position of the drug administration information 118, 142 on the port cradle 100 and SLCU 120.

The drug administration information 118, 142 and drug administration data are stored in the storage device 164 within the scanner module 156 or, for example, a magnetic card. However, the information and data may be uploaded to a remote storage device such as a centralized computer within a hospital or other medical facility. In addition, the information and data can be uploaded to multiple sites within a hospital or doctor facilities for administrative or diagnostic purposes.

Figure 12:
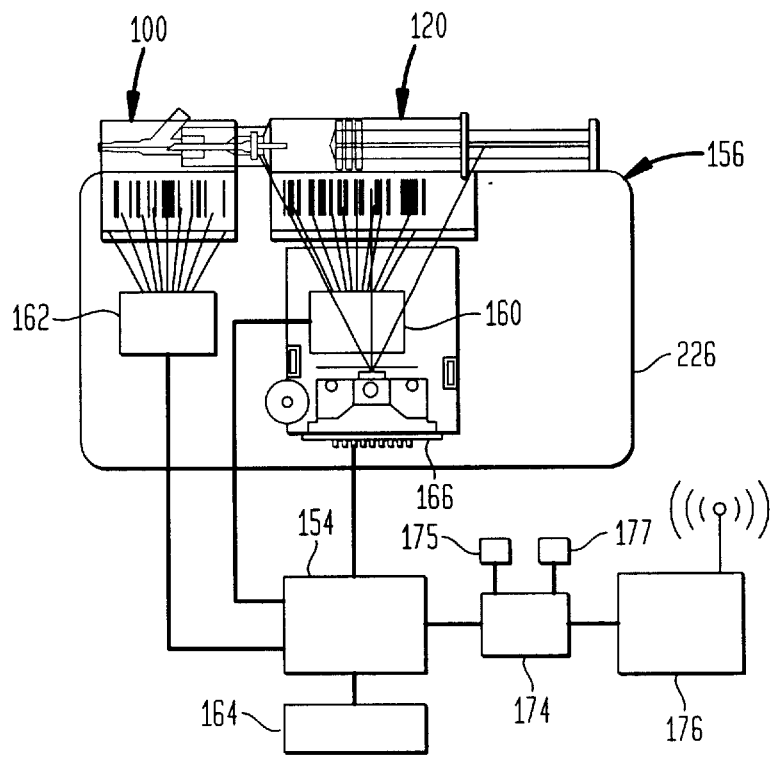
FIG. 12 is a block diagram showing the flow of data from the detector modules to an onboard microprocessor, parallel to a serial converter and wireless transceiver.

As shown in FIG. 12, the microprocessor 154 is connected to an on-board parallel to serial converter 174 and to a wireless transceiver 176. In the preferred embodiment, the microprocessor 154 will be coupled to a Universal Synchronis/Asynchronis Receiver/Transmitter for uploading and downloading information and data from the scanner module 156. It is further contemplated that the scanner module 156 may be connected to a modem 175 for transmitting the information and data over a telephone line, as well as providing a direct pin connection 177 for transmission of the information and data over a cable line to a network facility. The information and data can also be uploaded to a local PC workstation, and subsequently transmitted to remote locations. A more detailed description is disclosed in U.S. Pat. No. 5,651,775.

Figure 13A:
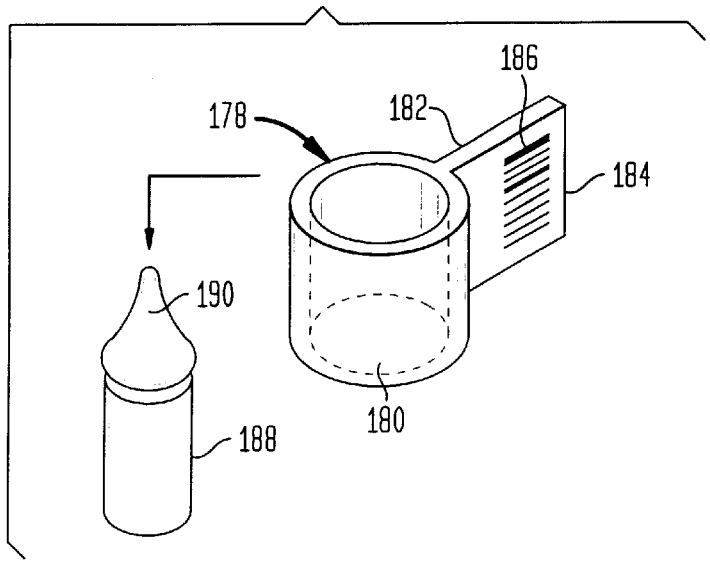
FIGS. 13A–13C are sequential views showing the attachment of a drug cradle to an ampule supply vessel.
Figure 13B:
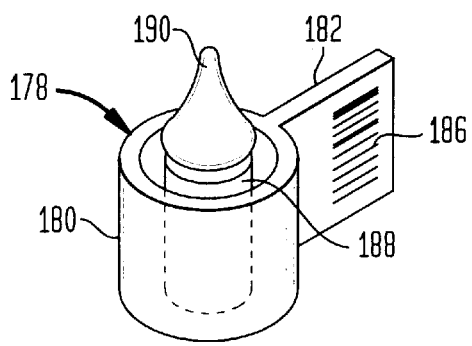
Figure 13C:
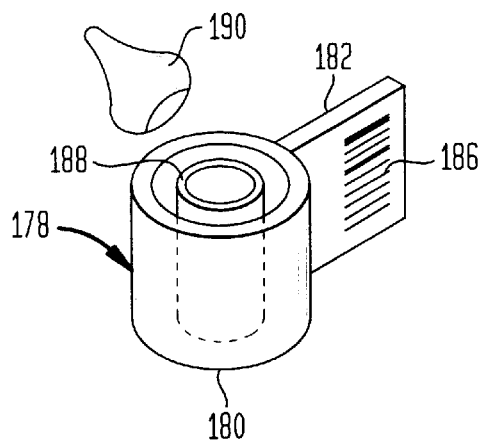

The scanner modules 144, 156 can be further used to load a syringe 124 with the appropriate drug to be administered and to keep a record thereof. As shown in FIGS. 13A–13C, there is provided a drug container cradle 178 constructed from a housing 180 from which there extends a planar flange 182 having a slider member 184 at its terminal end. The drug container cradle 178 may be constructed in a similar manner as port cradle 100. Drug administration information 186, e.g., in machine and/or human readable form, is provided on the drug container cradle 178, and preferably on flange 182 in the form of a label. The housing 180 provides a hollow interior for securing a drug ampule 188 therein. Any suitable means, such as friction fit, interfering ribs, adhesives and the like can be used to secure the ampule 188 within the drug container cradle 178. The top 190 of the ampule can be removed to provide access to the ampule's contents.

Figure 14A:
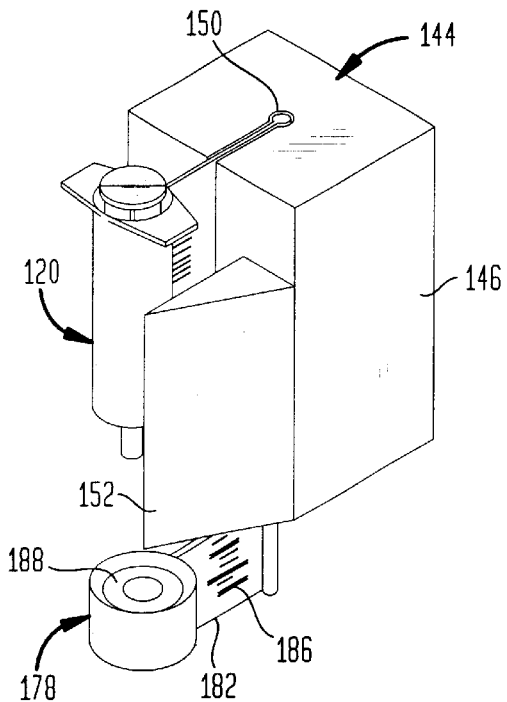
FIGS. 14A–14D are sequential views showing loading of the drug cradle containing a drug ampule into the scanner module containing a syringe label cradle unit for filling the syringe with the contained drug.
Figure 14B:
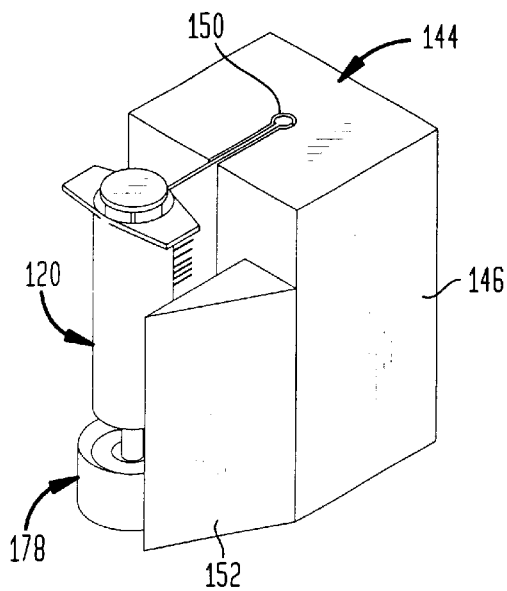
Figure 14C:
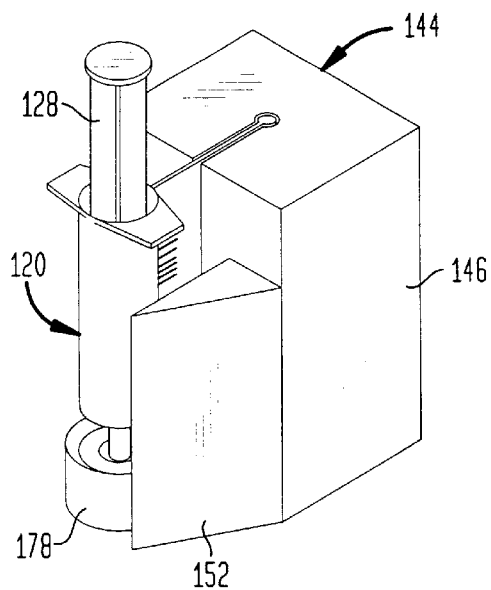
Figure 14D:
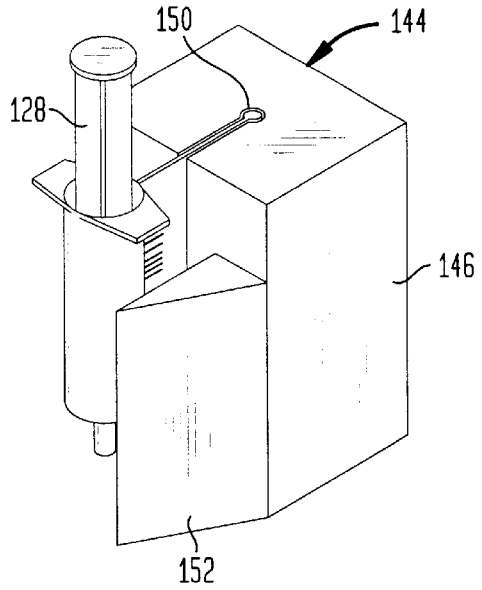

The drug administration information 186 may be similar to drug administration information 118, 142. The drug administration information 186 is scanned prior to loading a syringe 124 in a similar manner with respect to the previously described use of the port cradle 100. As shown in FIGS. 14A–14D, the drug container cradle 178 and SLCU 120 are supported by the scanner module 144 or 156. When supported by the scanner module 144, the needle 126 of the syringe 124 is aligned with the opening in the ampule 188 as supported by the drug container cradle 178. The ampule 188 after removing top 190 is open and unsealed. As a result, the drug container cradle 178 should be maintained in a vertical orientation to avoid spilling of the contained drug. Drug administration information 186 is read from the drug container cradle 178 and stored within the storage device 164. The information can include the foregoing information as previously described with respect to drug administration information 118, 142. Thus, the syringe 124 will be a smart syringe by having its content and patient recipient identified by operation of the scanner module 146. After loading the syringe 124, the drug container cradle 178 can be removed from the scanner module 156 as shown in FIG. 14D. The scanner module 146, with loaded syringe 124 is now ready for drug administration via a port cradle 100.

Figure 15A:
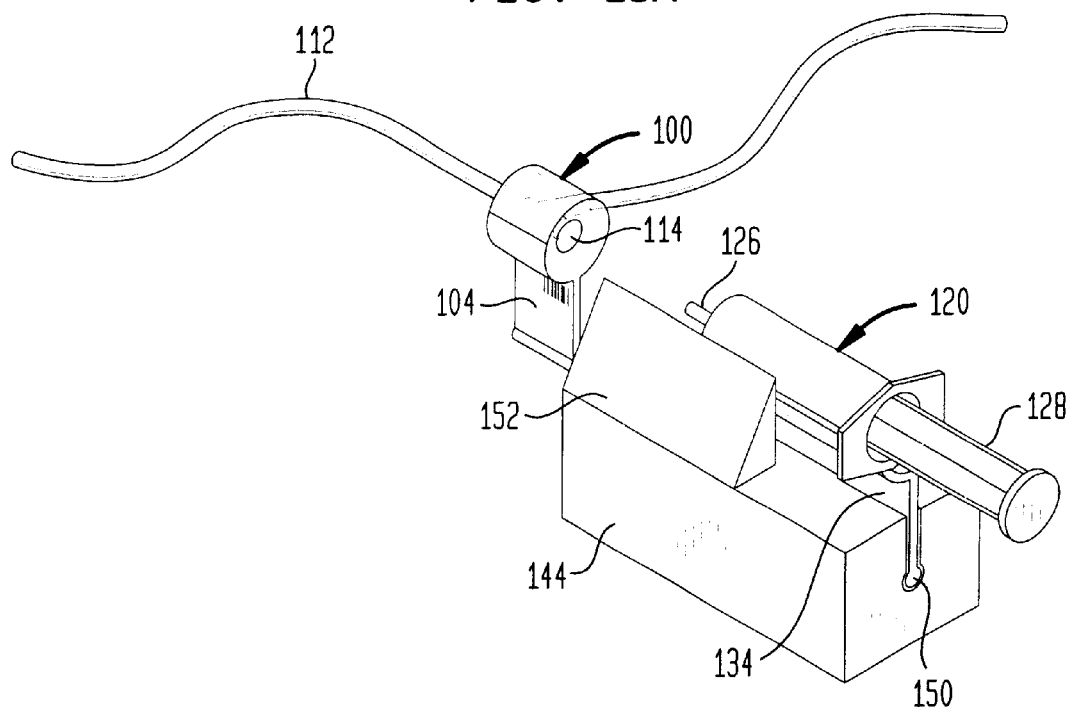
FIGS. 15A–15B are sequential views showing the alignment of the port cradle with a drug loaded syringe using the scanner module.
Figure 15B:
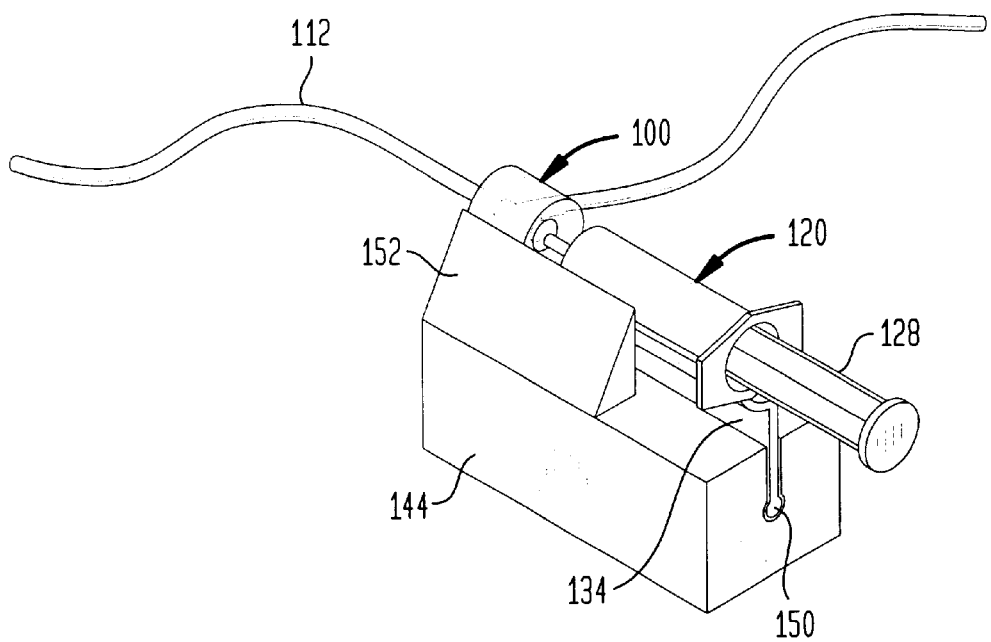

As shown in FIGS. 15A–15B, a port cradle 100 can be mounted to the scanner module 144 in alignment with the loaded syringe 124. Drug administration information 118, 142 and drug administration data can be recorded during drug administration as thus far described.

Figure 16A:
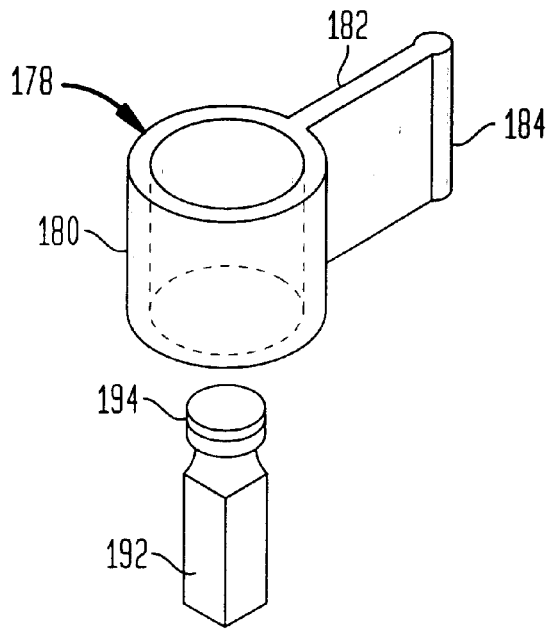
FIGS. 16A–16C are sequential views showing a drug cradle mounted onto a drug vial, the vial cap being removed to expose the septum for syringe needle insertion.
Figure 16B:
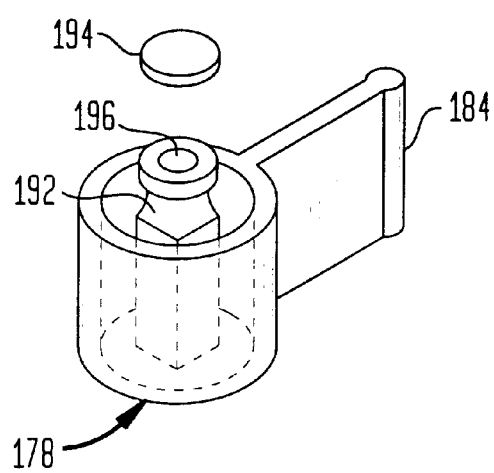
Figure 16C:
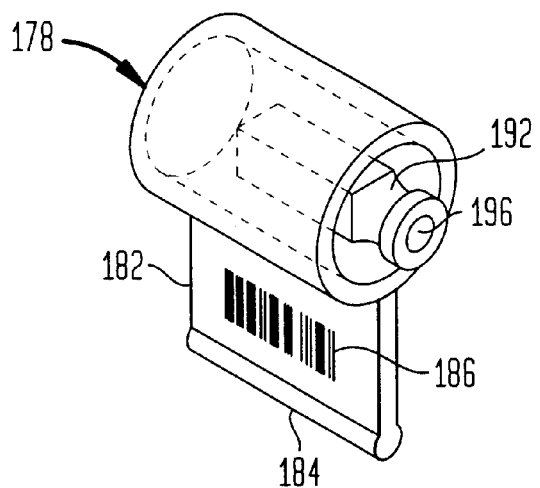
Figure 18:
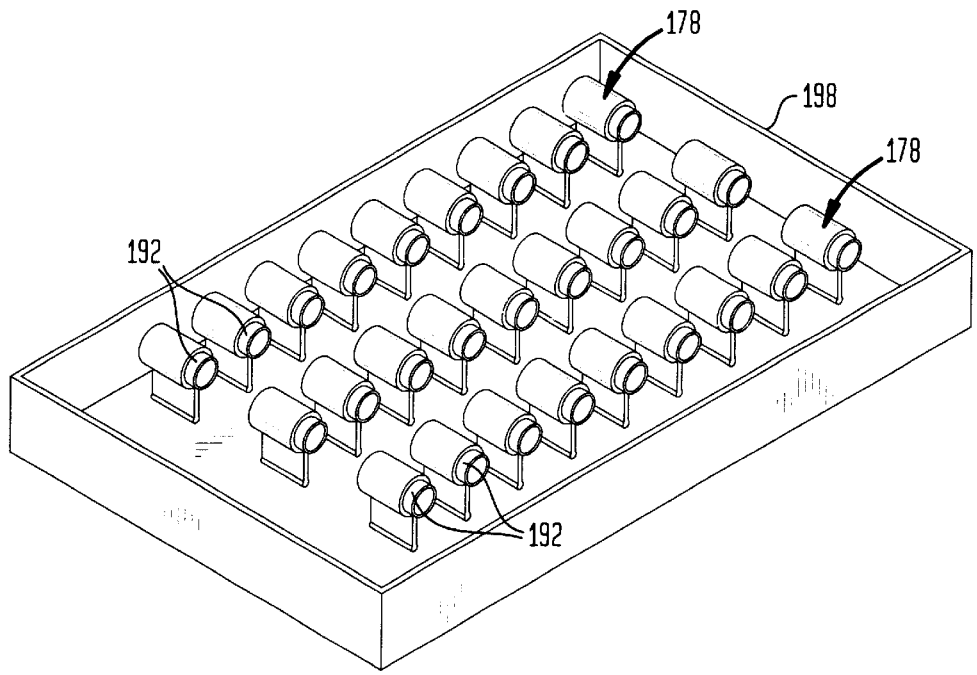
FIG. 18 is a perspective view showing multiple drug cradles holding drug ampules or drug vials arranged in an organized matrix within a support container.

With reference to FIGS. 16A–16C, the drug container cradle 178 is operative for securing a drug vial 192. Upon removing cap 194, the septum 196 of the drug vial 192 is exposed. The syringe 124 can be loaded with a drug as shown in FIGS. 17A–17B. The loading of the syringe 124 from a drug vial 192 is similar to loading the syringe from an ampule 188. As the drug vial 192 is provided with a septum 196, it is not required that the drug vial 192 be arranged facing upwardly. As shown, the drug vial 192 may be arranged facing downwardly in a general vertical direction as is conventional when loading syringes. The loading of the syringe 124 in a vertical direction is preferred from ampules 188 and drug vials 192 as it minimizes the possibility of withdrawing air into the syringe. The co-joining of the drug vial 192 and the syringe 124 is digitally documented by the detector module 152 to record the appropriate drug administration information obtained from the drug container cradle 178 and SLCU 120 as previously described. Pre-loaded drug container cradles 178 can be stored in a container 198 for subsequent use as shown in FIG. 18. Each container 198 may house a plurality of drugs of the same type, or drugs for a particular patient. Thus, loading of syringes 124 can be achieved in an efficient and effective manner using a scanner module 144, 156 in accordance with the present invention.

Figure 19:
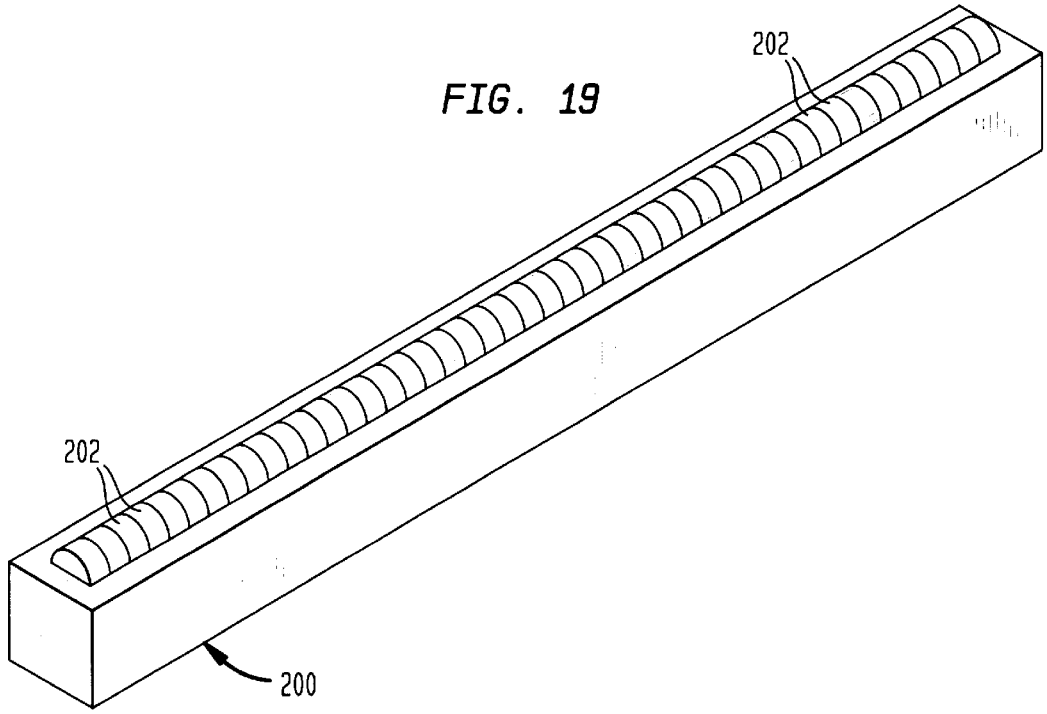
FIG. 19 is a perspective view of a linear CCD device constructed from a series of photo cells.
Figure 20:
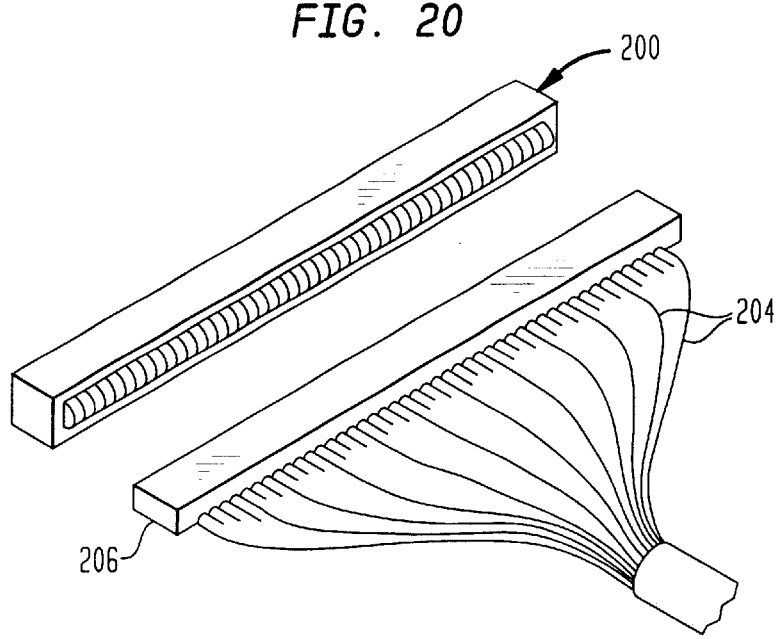
FIG. 20 is a perspective view showing a linear CCD device aligned with a flat ribbon of photo optic fiber elements.
Figure 21:
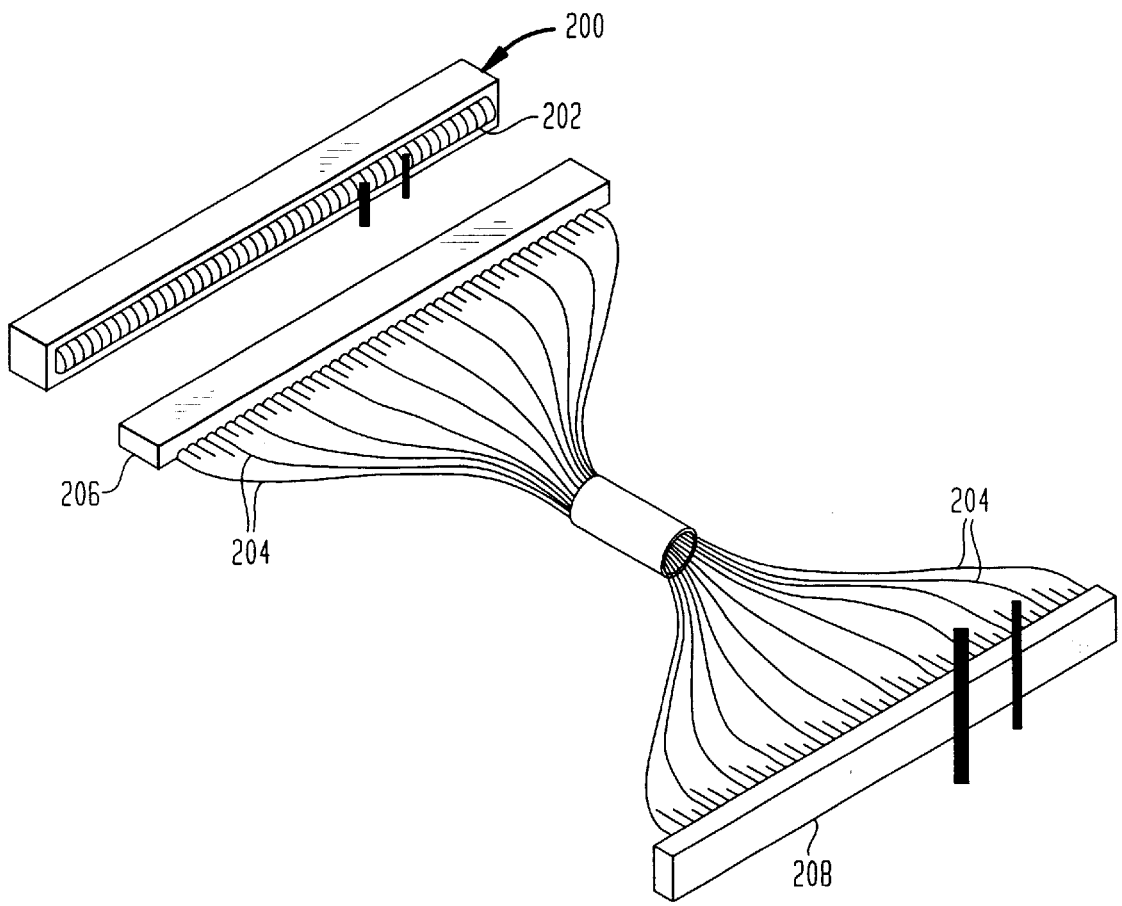
FIG. 21 is a perspective view showing a one-to-one correspondence between each photo cell of the CCD array and a fiber optic filament.

There will now be described the construction of the detectors 160, 162, 166 using linear CCD devices and fiber optics. As diagrammatically shown in FIG. 19, a detector includes a linear CCD device 200 which functionally form a linear long series of photocells 202 which respond to light and dark levels. In general, a CCD is a semiconductor device that converts optical images into electrical signals. As shown in FIG. 20, a flat ribbon of individual fiber optic filaments 204 is terminated at one end in a connecter 206. Each of the fiber optic filaments 204 conducts light along its length emitted from its opposite end. The fiber optic filaments 204 terminate in the connector 206 in correspondence with the individual photocells 202 in the CCD device 200. The other end of the fiber optic filaments 204 also terminate in a connector 208 as shown in FIG. 21. The ends of the fiber optic filaments 204 in the connectors 206, 208 are in positional one-to-one correspondence with one another. In other words, light entering, for example, the third filament in connector 208 will emanate at the same position within connector 206. The connector 206 is positioned facing the photocells 202 within the CCD device 200. There is accordingly positional relationship between the fiber optic filaments 204 and the photocells 202. Thus, light received at connector 208 will be sensed by a photocell 202 at the same position that the light enters connector 208. It is contemplated that more than one fiber optic filament 204 may be associated with a single photocell 202. In addition, more than one photocell 202 may be associated with more than one fiber optic filament 204. Further, a number of photocells 202 may be associated with a plurality of fiber optic filaments 204. In any event, there is generally a positional relationship between light entering connector 208 and a responding photocell 202 within the CCD device 200.

Figure 22:
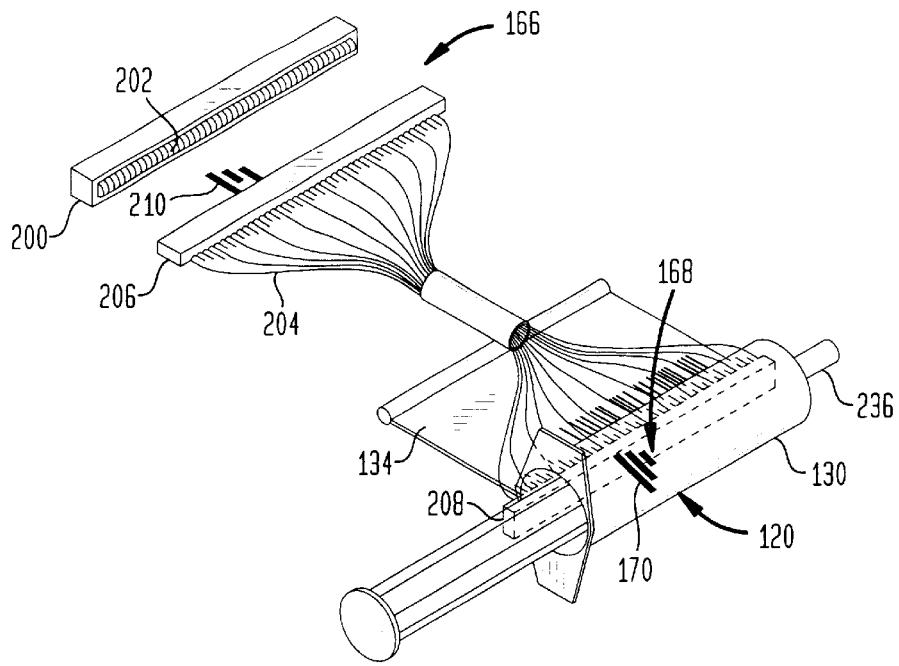
FIG. 22 is a perspective view showing the relationship between the linear CCD device and fiber optic filaments in operative alignment and association with a syringe label cradle unit.
Figure 23:
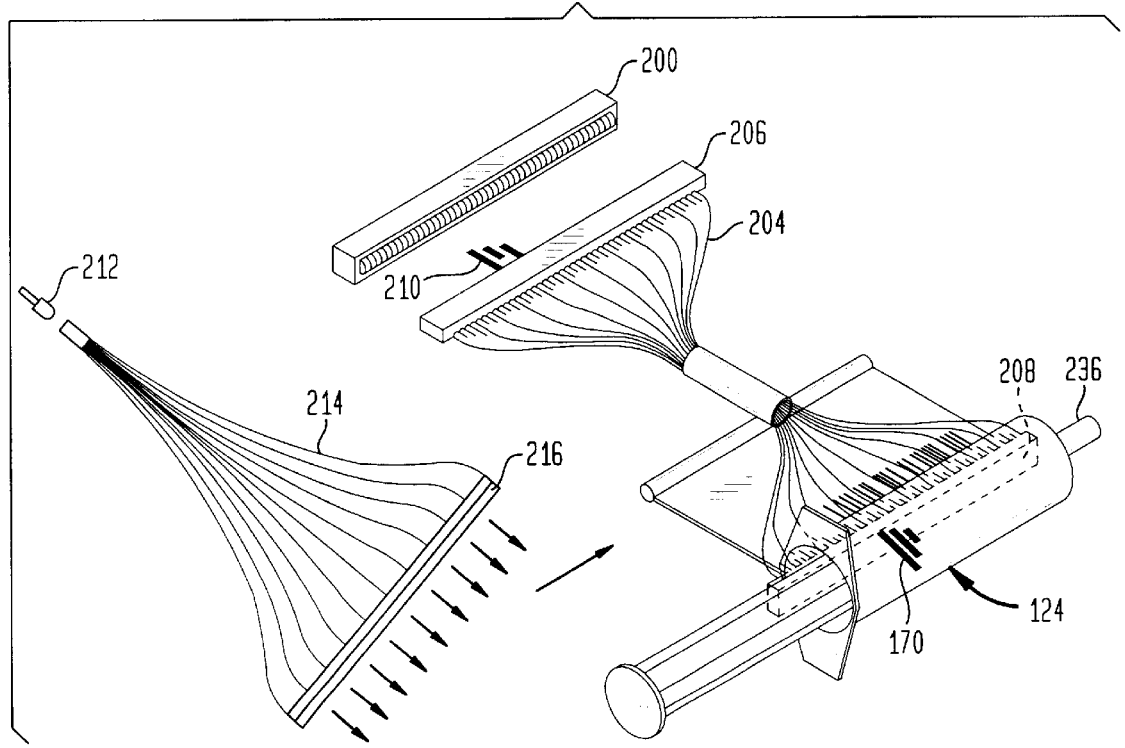
FIG. 23 is a perspective view showing the use of fiber optic filaments as an illumination source for the syringe label cradle unit.

Referring to FIG. 22, the detector 166 is constructed by positioning connector 208 within the scanner module 156 at a location facing and in alignment with the location of the syringe barrel 130 when supported by the scanner module. Dark portions corresponding to the plunger tip seal 168 and its edge 170 are detectable as similar dark portions at corresponding photocells 202 within the CCD device 200. These dark portions which are detected by the photocells 202 are diagrammatically identified by element 210, i.e., corresponding to the plunger tip seal 168 and edge 170. Illumination to the syringe 124 at the connector 208 can be effected using a light source 212. The light source 212 may be directed in one-to-one correspondence to the fiber optic filaments 204 at the connector 208 using a similar fiber optic bundle 214 and connector 216 as shown in FIG. 23. However, any other form of a light source, including normal room lighting may be used.

Figure 24:
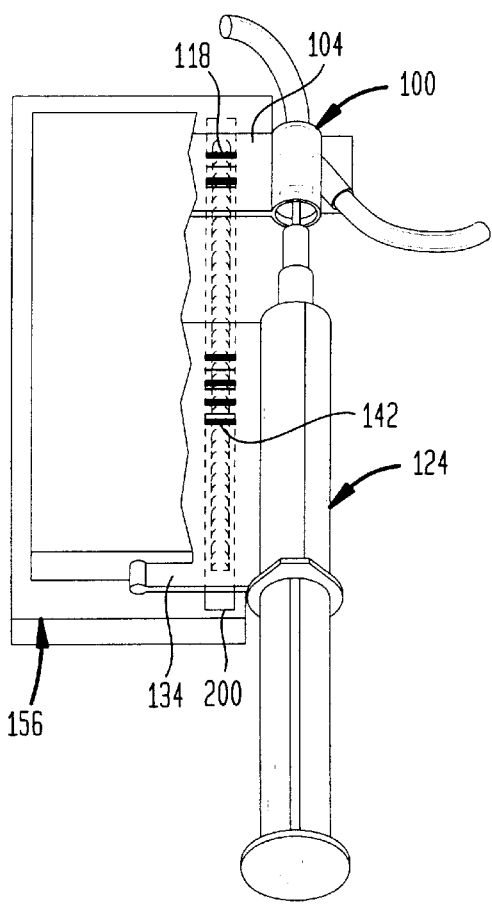
FIG. 24 is a perspective view showing the operative position of a linear CCD device in the scanner module in alignment with the machine readable bar code on the port cradle and syringe label cradle unit.
Figure 25:
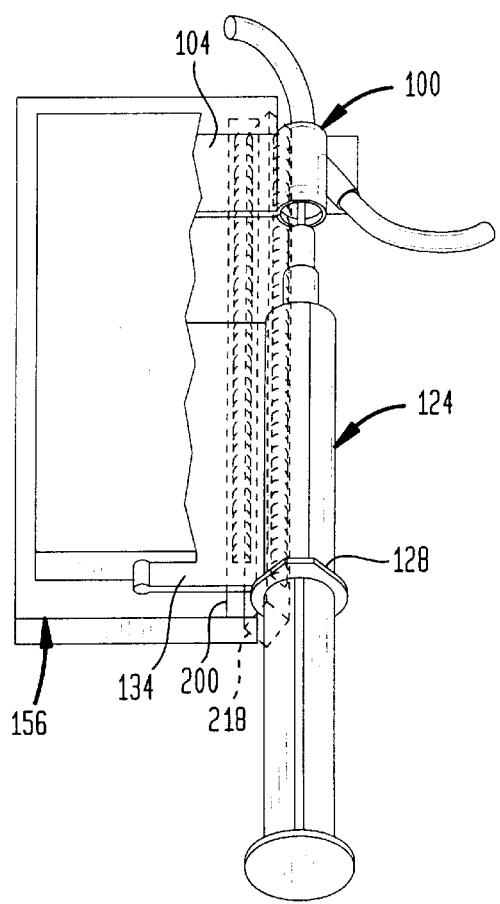
FIG. 25 is a perspective view showing a second linear CCD device within the scanner module arranged in alignment with the barrel and plunger of the syringe.

Turning to FIG. 24, it is not a requirement of the present invention that a bundle of fiber optic filaments 204 be used for transmitting images or other data to the CCD device 200. In particular, the CCD device 200 may be positioned directly in alignment for detecting movement of the plunger 128 as well as reading the drug administration information 118 on the port cradle 100 and the drug administration information 142 on the syringe 124. Accordingly, as the port cradle 100 and syringe 124 are inserted into the scanner module 156, their respective drug administration information 118, 142, in the nature of machine readable barcodes, are read by the CCD device 200. In a similar manner, as shown in FIG. 25, a CCD device 218 can be positioned within the scanner module 156 to directly detect movement of the plunger 128 within the syringe 124. Drug administration data obtained from the movement of the plunger 128 during drug administration is detected by the CCD device 218 as previously described.

In accordance with the preferred embodiment, the CCD devices 200, 218 are located within the body of the scanner module 156 remote from the port cradle 100, syringe 128 and drug administration information 118, 142. The drug administration information and drug administration data are transmitted to the CCD devices 200, 218 by means of a bundle of fiber optic filaments 204 as previously described. By positioning the CCD devices 200, 218 remote from the syringe 124 and port cradle 100, this isolates the electronic circuitry required for the operation of the CCD devices from any potential spillage of drugs from the syringe or port cradle during drug administration.

Figure 26:
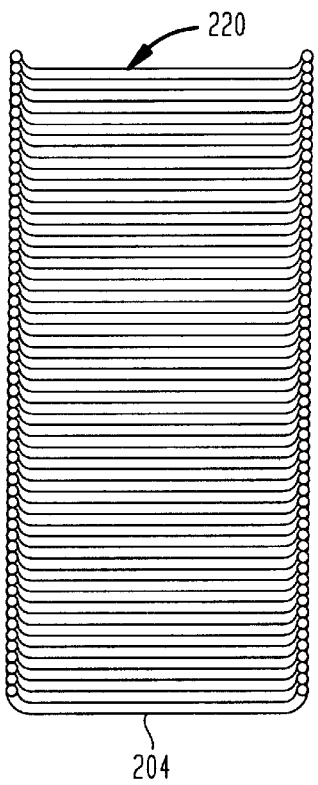
FIG. 26 is a top plan view of a fiber optic bundle forming a linear array of fiber optic filaments.

As shown in FIG. 26, the fiber optic filaments 204 may be adhered together such as by use of an adhesive to form a fiber optic ribbon 220. The use of a fiber optic ribbon 220 facilitates positioning of the individual fiber optic filaments at their input end in proper alignment within the scanner module 156 and with respect to a CCD device at their output end. However, a connector, such as connector 208 as previously described may also be used to facilitate the alignment.

Figure 27A:
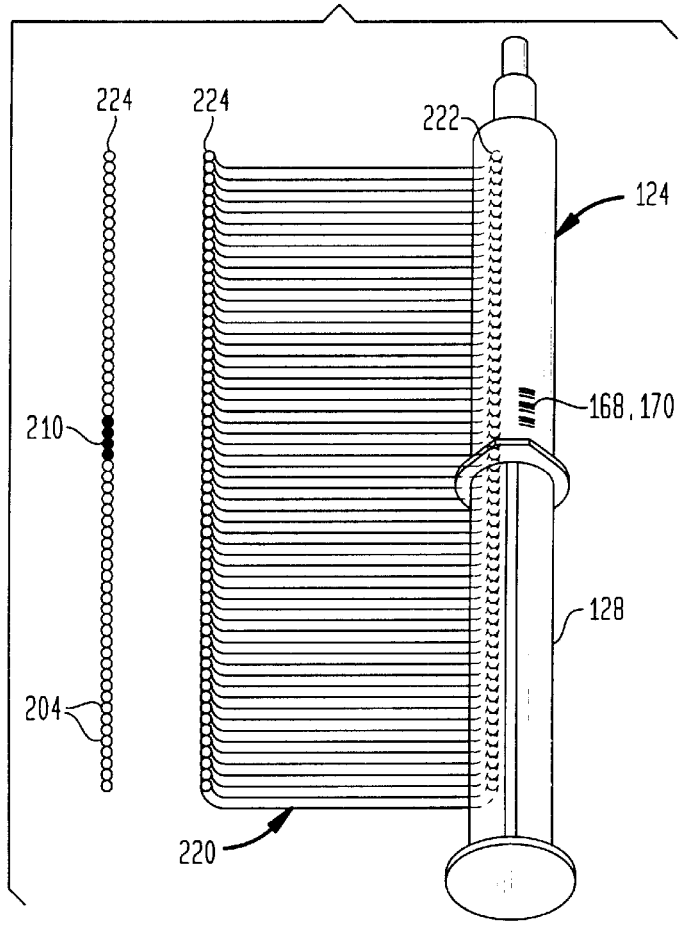

As shown in FIGS. 27A–27B, the input end 222 of the fiber optic ribbon 220 is positioned to scan movement of the plunger 128 for detecting the location of the plunger tip seal 168 and/or edge 170. Detection of the movement of the plunger tip seal 168 or edge 170 is diagrammatically identified by element 210 at the output end 224 of the fiber optic ribbon 220. Accordingly, the distance of movement of the plunger 124 can be determined to calculate the volume of drug being administered by the syringe 124 which is of known size.

Referring to FIG. 28, a first fiber optic ribbon 220 is positioned within the scanner module 156 having its input end 222 arranged in alignment for reading the drug administration information 118, 142 on the port cradle 100 and syringe 124. The output end 224 of the fiber optic ribbon 220 is aligned with a CCD device 200 which is positioned remote from the location of the syringe 124 and port cradle 100. In a similar manner as shown in FIG. 29, a second fiber optic ribbon 220 is arranged within the scanner module 156 having its input end 222 facing the plunger 128 of the syringe 124. The output end 222 of the second fiber optic ribbon 220 is connected to a CCD device 218 for detecting movement of the plunger 128 as previously described for determining the amount of drug administered in real time. The components of the scanner module 156, as thus far described, may be contained within a housing 226 which may be ergonomically designed for ease of hand holdability and portability to the patient sites for use.

Figure 30:
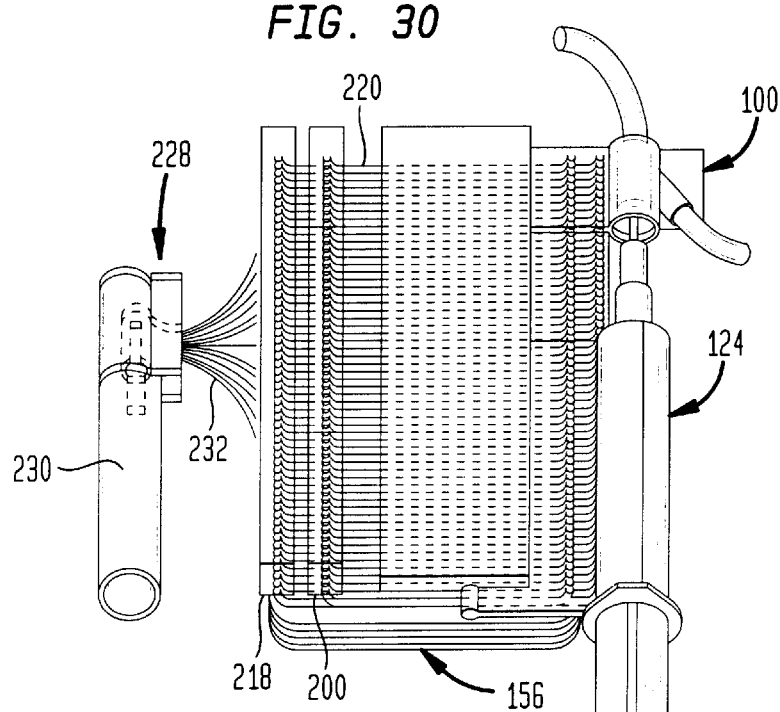
FIG. 30 is a perspective view showing the assembly as shown in FIG. 29 in operative association with a fiber optic ribbon light source for illuminating the machine readable bar code on the port cradle and syringe label cradle unit, and the barrel of the syringe for determining plunger movement.
Figure 31:
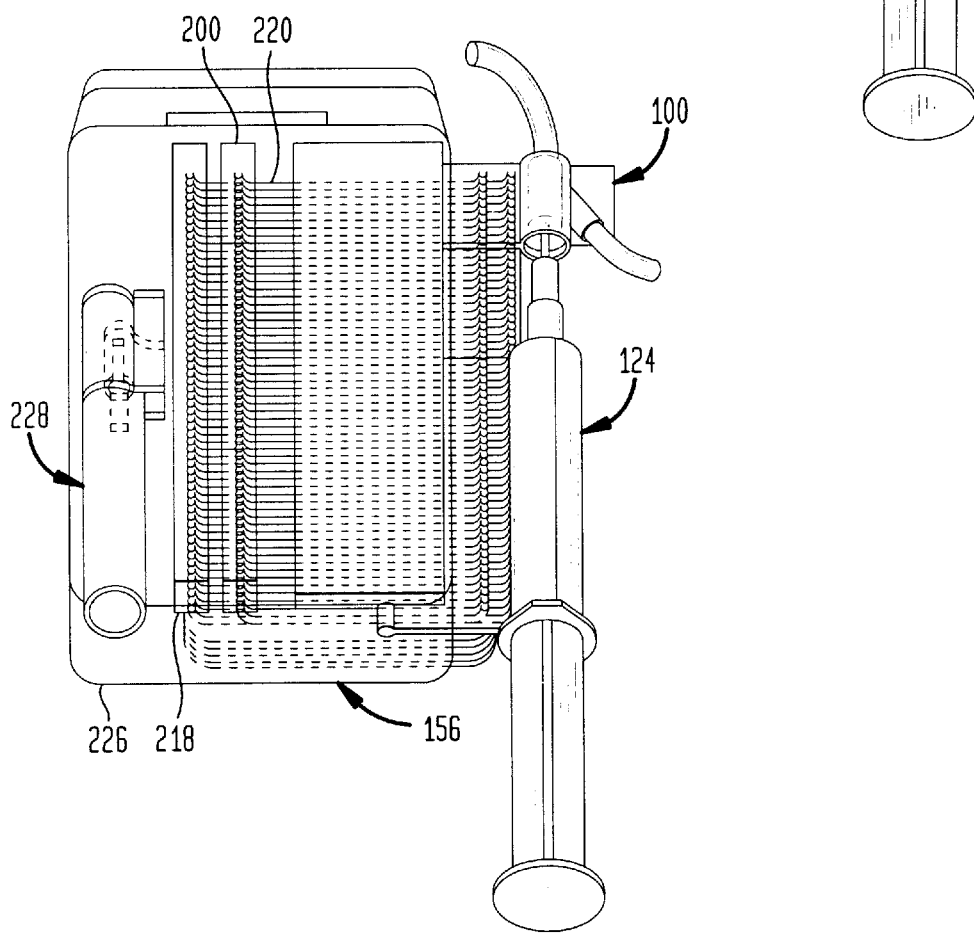
FIG. 31 is a perspective view showing the assembly of FIG. 30 within a housing forming the scanner module.

Referring to FIGS. 30 and 31, the drug administration information 118, 142 on the port cradle 100 and syringe 124, including the plunger 128 of the syringe 124 may be illuminated by an illumination device 228. The illumination device 228 may include a powered light source such as a bulb or laser device and batteries within a housing 230. Light from the illumination device 228 is transmitted via fiber optic bundle 232. The illumination device 228 is contained within the housing 226 of the scanner module 156.

Figure 32:
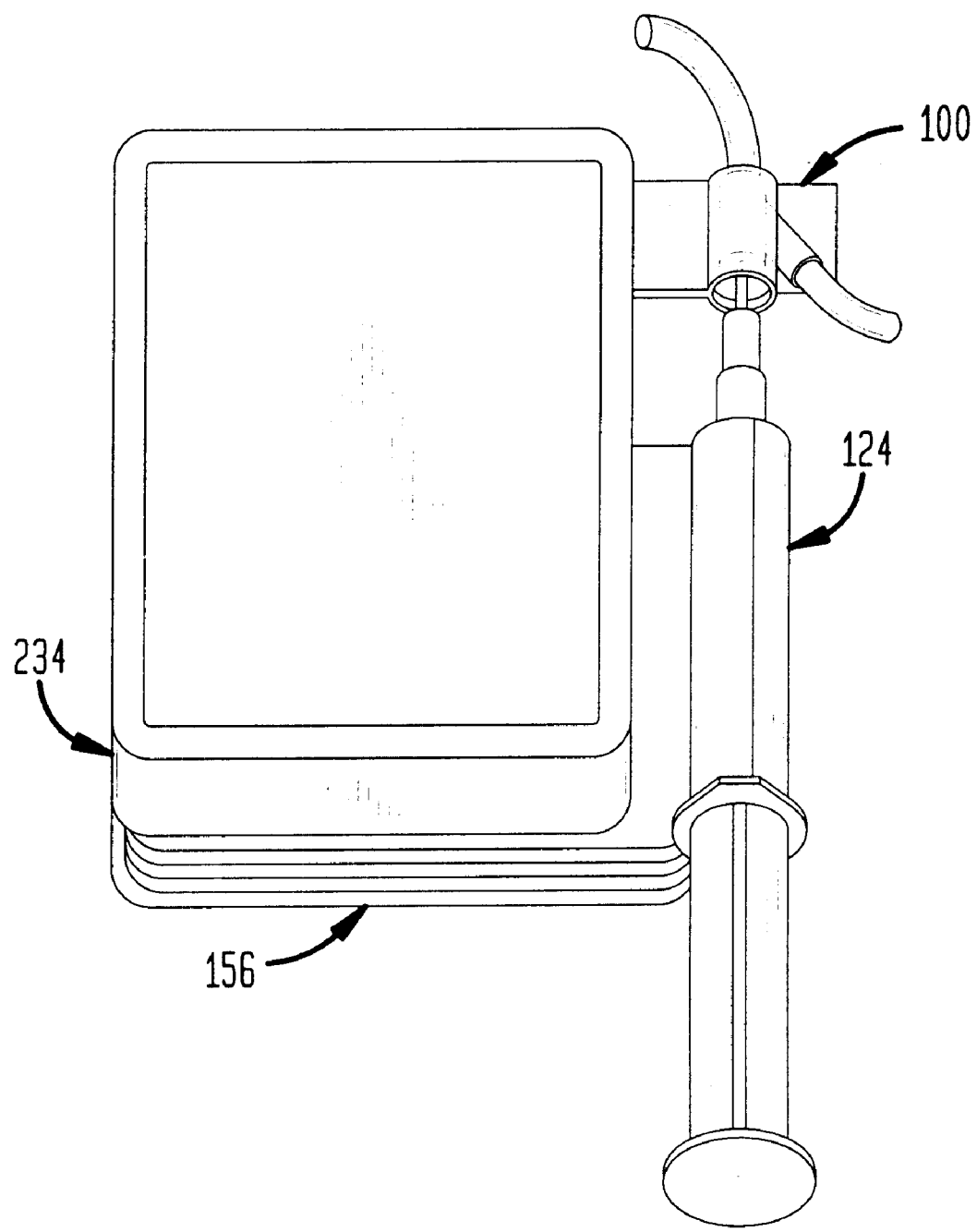
FIG. 32 is a perspective view of the scanner module as shown in FIG. 31 in operative association with a personal information manager for uploading and downloading information thereto.

Turning to FIG. 32, the scanner module 156 may be connected to a personal digital assistant, personal information manager or other such system for downloading the drug administration information and drug administration data from the scanner module 156. By way of example, a Palm Pilot 234 or other such personal digital assistant or personal information manager may be used. The device 234 may be removed from the scanner module 156 for uploading to a local or remote computer either directly or through a network, as well as using a modem or other form of transceiver, including an infrared link.

Referring once again to FIG. 8, the port cradle 100 generally includes a cylindrical housing 102 having an open end which exposes the septum 114 of the injection port 110. Although preferably of cylindrical shape, the housing 102 may have other shapes such as oval, triangular, rectangular, polygonal and the like. The syringe 124 is provided with a safety shield 236 which extends from the barrel 130 of the syringe outwardly to a length generally greater than the length of the needle 126, see FIG. 5. The safety shield 236 prevents inadvertent contact with the needle 126 when handling the syringe 124 by a technician and during drug administration. In addition to preventing injury to the technician, it also prevents contamination of the needle tip.

The safety shield 236 will have a corresponding cross-sectional shape as the housing 102 of the port cradle 100. In accordance with one embodiment, the outside diameter of the safety shield 236 is slightly less than the inside diameter of the housing 102 of the port cradle 100. As a result, the safety shield 236 will slide or telescope into the interior of the housing 102 where it surrounds the septum 114 of the injection port 110. This arrangement effectively interlocks the syringe 124 with the port cradle 100 to prevent access to either the needle 126 or septum 114 which prevents contamination, as well as ensuring alignment of the needle with the septum. Conversely, the housing 102 may be sized to be telescopically or slidingly received within the interior of the safety shield 236. In a similar manner, the safety shield 236 may nest or telescope within the opening formed by the drug container cradle 178.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A drug delivery and monitoring system comprising a scanner module including a first and second detector module, said first detector module determining drug administration data and identifying first drug administration information, said second detector module identifying second drug administration information, said scanner module including a storage device for storing said data and said first and second information; a syringe including a barrel and a plunger moveable therein for administration of a drug, said syringe having said first drug administration information provided in association therewith, said syringe constructed to be releasably attached to said scanner module in operative association with said first detector module, whereby movement of said syringe relative to said first detector module causes said first detector module to identify said first drug administration information for storage in said storage device and movement of said plunger within said barrel causes said first detector module to determine said drug administration data for storage in said storage device; a port cradle attachable to an injection port, said cradle having said second drug administration information provided in association therewith, said cradle constructed to be releasably attached to said scanner module in operative association with said second detector module, whereby movement of said cradle relative to said second detector module causes said second detector module to identify said second drug administration information for storage in said storage device.

2. The system of claim 1, further including a microprocessor in operative association with said first and second detector modules and said storage device.

3. The system of claim 2, further including a transceiver in operative association with said microprocessor for transmitting said drug administration data and said first and second drug administration information to a remote location.

4. The system of claim 2, further including a modem in operative association with said microprocessor for transmitting said drug administration data and said first and second drug administration information to a remote location.

5. The system of claim 2, further including a connector in operative association with said microprocessor for transmitting said drug administration data and said first and second drug administration information to a remote location.

6. The system of claim 1, wherein said storage device is removably insertable into said scanner module.

7. The system of claim 1, wherein said first detector module comprises a pair of detectors.

8. The system of claim 1, wherein said detector modules comprise a photo sensing electronic detector and a fiberoptic array for carrying said drug administration data and said drug administration information.

9. The system of claim 1, wherein said second detector module comprises a single detector.

10. The system of claim 1, wherein said first detector module determines the amount of a drug being administered by said syringe in real time in the form of said drug administration data for storage in said storage device.

11. The system of claim 1, wherein said port cradle comprises a holder surrounding said injection port and a flange extending therefrom.

12. The system of claim 11, wherein said scanner module includes a slotted opening for slidingly receiving said flange therein for releasably attaching said port cradle to said scanner module.

13. The system of claim 11, wherein said second drug administration information is provided on said flange.

14. The system of claim 11, wherein said syringe includes a flange extending therefrom, said first drug administration information provided on said flange.

15. The system of claim 14, wherein said scanner module includes a slotted opening for slidably receiving said flange therein for releasably attaching said syringe to said scanner module, said syringe having a needle in alignment with said injector port when said port cradle is attached to said scanner module.

16. The system of claim 1, further including a drug container cradle attachable to a drug container, said drug container cradle having third drug administration information provided in association therewith, said drug container cradle constructed to be releasably attached to said scanner module in operative association with said second detector module, whereby movement of said drug container cradle relative to said second detector module causes said second detector module to identify said third drug administration information for storage in said storage device.

17. The system of claim 16, wherein said drug container cradle comprises a holder surrounding said drug container and a flange extending therefrom.

18. The system of claim 17, wherein said third drug administration information is provided on said flange.

19. A drug delivery and monitoring system comprising a scanner module including a first and second detector module, said first detector module determining drug administration data and identifying first drug administration information, said second detector module identifying second drug administration information, said scanner module including a storage device for storing said data and said first and second information; a syringe including a barrel having a flange extending therefrom and a plunger moveable therein for administration of a drug, said syringe having said first drug administration information provided on said flange, said scanner module constructed to slidingly receive said flange of said syringe in operative association with said first detector module, whereby movement of said syringe relative to said first detector module causes said first detector module to identify said first drug administration information for storage in said storage device and movement of said plunger within said barrel causes said first detector module to determine said drug administration data for storage in said storage device; a port cradle having a flange extending therefrom attachable to an injection port, said cradle having said second drug administration information provided on said flange thereof, said scanner module constructed to slidingly receive said flange of said cradle in operative association with said second detector module, whereby movement of said cradle relative to said second detector module causes said second detector module to identify said second drug administration information for storage in said storage device; a microprocessor in operative association with said first and second detector modules and said storage device.

20. The system of claim 19, further including a transceiver in operative association with said microprocessor for transmitting said drug administration data and said first and second drug administration information to a remote location.

21. The system of claim 19, further including a drug container cradle attachable to a drug container, said drug container cradle having third drug administration information provided in association therewith, said drug container cradle constructed to be releasably attached to said scanner module in operative association with said second detector module, whereby movement of said drug container cradle relative to said second detector module causes said second detector module to identify said third drug administration information for storage in said storage device.

22. The system of claim 19, wherein said detector modules comprise a photo sensing electronic detector and a fiber optic array for carrying said drug administration data and said drug administration information.

23. A cradle coupled to a drug container, said cradle comprising a housing having an opening attached about a drug container having a drug therein to be administered to a patient, said drug container including a septum accessible through said opening for piercing by a needle attached to a syringe for filling said syringe with said drug, and a flange extending from said housing, said cradle adapted for supporting thereon drug administration information.

24. The cradle of claim 23, wherein said drug administration information is provided on said flange.

25. The cradle of claim 23, wherein said housing has a tubular shape with open ends defining an interior, said drug container attachable to said housing within said interior thereof.

26. A cradle coupled to an injection port, said cradle comprising a housing coupled to an injection port and a flange extending therefrom, said cradle adapted for supporting thereon drug administration information.

27. The cradle of claim 26, wherein said drug administration information is in machine readable form.

28. The cradle of claim 26, wherein said housing includes an opening and said injection port includes a septum accessible through said opening for piercing by a needle attached to a syringe.

29. The cradle of claim 26, wherein said housing has a tubular shape with open ends defining an interior, said injection port contained within said interior thereof.

30. A method for monitoring drug delivery to an injection port, said method comprising positioning a scanner module adjacent an injection port, said scanner module including first and second detector modules, said first detector module determining drug administration data and identifying first drug administration information, said second detector module identifying second drug administration information, said scanner module including a storage device for storing said data and said first and second information; releasably securing a syringe loaded with a drug to be administered to said scanner module, said syringe having said first drug administration information provided in association therewith, identifying said first drug administration information by said first detector module, releasably securing a port cradle attached to an injection port to said scanner module, said port cradle having said second drug administration information provided in association therewith, identifying said second drug administration information by said second module detector, determining said drug administration data by said first detector module regarding the drug being delivered from said syringe to said injection port, and storing in said scanner module said first and second drug administration information and said drug administration data.

31. The method of claim 30, wherein said drug administration data comprises the amount of said drug delivered by said syringe.

32. The method of claim 30, further including transmitting said stored first and second drug administration information and said drug administration data to a storage device other than in said scanner module.

33. The method of claim 30, wherein said port cradle includes a flange extending therefrom and said scanner module includes a slotted opening for slidingly receiving said flange, wherein said identifying said second drug administration information comprises inserting said flange into said slotted opening and moving said port cradle into operative association with said second detector module.

34. The method of claim 33, wherein said second drug administration information is provided on said flange.

35. The method of claim 30, wherein said syringe includes a plunger for delivering said drug therefrom and wherein said determining said drug administration data comprises determining the distance of movement of said plunger within said syringe during drug delivery.

36. The method of claim 35, wherein said determining said drug administration data occurs in real time.

37. The method of claim 30, further including providing a drug container cradle attached to a drug container, said drug container cradle having third drug administration information provided in association therewith, said drug container cradle constructed to be releasably attached to said scanner module in operative association with said second detector module, and displacing said drug container cradle relative to said second detector module to identify said third drug administration information by said second detector module, and inserting a needle extending from said syringe into said drug container for filling said syringe with said drug.

38. The method of claim 30, wherein said first detector module comprises a first detector for determining said drug administration data and a second detector for identifying said first drug administration information.

39. The method of claim 30, further including monitoring drug delivery to a plurality of patients using the same scanner module.

40. A method for monitoring drug delivery to an injection port, said method comprising positioning a scanner module adjacent an injection port in fluid communication with a patient, said scanner module including first and second detector modules, said first detector module determining drug administration data and identifying first drug administration information, said second detector module identifying second drug administration information, said scanner module including a storage device for storing said data and said first and second information; releasably securing a syringe loaded with a drug to be administered to said scanner module, said syringe including a flange having said first drug administration information provided thereon, moving said flange of said syringe into operative association with said first detector module, identifying said first drug administration information by said first detector module, releasably securing a port cradle attached to an injection port to said scanner module, said port cradle including a flange having said second drug administration information provided thereon, making said flange of said port cradle into operative association with said second detector module, identifying said second drug administration information by said second detector module, determining said drug administration data by said first detector module regarding the drug being delivered from said syringe to said injection port, wherein said syringe includes a plunger for delivering said drug therefrom and wherein said determining said drug administration data comprises determining the distance of movement of said plunger within said syringe during drug delivery and storing in said scanner module said first and second drug administration information and said drug administration data.

41. The method of claim 40, wherein said first and second drug administration information includes patient information.

42. The method of claim 40, further including providing a drug container cradle attached to a drug container, said drug container cradle having third drug administration information provided in association therewith, said drug container cradle constructed to be releasably attached to said scanner module in operative association with said second detector module, and displacing said drug container cradle relative to said second detector module to identify said third drug administration information by said second detector module, and inserting a needle extending from said syringe into said drug container for filling said syringe with said drug.

43. The method of claim 40, further including transmitting said stored first and second drug administration information and said drug administration data to a storage device other than in said scanner module.

44. The method of claim 40, wherein said determining said drug administration data occurs in real time.

45. A method for delivering and monitoring drugs to an injection port connected to a patient, said method comprising delivering a needle on a drug loaded syringe to said injection port, automatically determining information relative to the drug contained in the syringe by electronically scanning machine readable information associated with said syringe, automatically determining information relative to the patient by electronically scanning machine readable information associated with said injection port, pushing a plunger of the syringe to deliver a quantity of the drug through the port, monitoring movement of the plunger while delivering the drug for determining the volume of the drug delivered from the syringe, and storing the patient information obtained by scanning said machine readable information and the quantity of the drug delivered from said syringe.

46. The method of claim 45, further including transmitting the stored patient information and the quantity of the drug delivered to a remote storage device.

47. The method of claim 45, further including attaching said injection port to a port cradle having a flange to which said machine readable information is attached, said electronically scanning said machine readable information comprising moving said flange past a photosensing electronic detector.

48. A method for delivering and monitoring drugs to an injection port connected to a patient, said method comprising delivering a needle on a drug loaded syringe into the injection port, automatically determining identification information relative to the drug contained in the syringe by electronically scanning a label, pushing a plunger of the syringe to deliver a volume of the drug through the inection port, automatically determining information relative to the patient by electronically scanning a label associated with the injection port, monitoring movement of the plunger for the purpose of calculating the amount of drug delivered, and storing the patient information and amount of the drug delivered.

49. The method of claim 48, further including transmitting the stored patient information and the quantity of the drug delivered to a remote storage device.

50. The method of claim 48, further including attaching said injection port to a port cradle having a flange to which said label is attached, said electronically scanning said label comprising moving said flange past a photosensing electronic detector.

51. A method of determining patient information before administering a drug from a syringe to an injection port connected to said patient, said method comprising providing said patient information in machine readable form on a cradle for said injection port, and scanning the machine readable information by an electronic detector for reading said patient information before administering said drug.

52. The method of claim 51, further including storing said patient information read by said scanning.

53. The method of claim 51, wherein said scanning comprises scanning a label adhered to a flange extending from said cradle.

54. The method of claim 53, further including sliding said flange through a slotted opening with a scanning module, said scanning module housing said detector.

55. The method of claim 51, further including transmitting said patient information read by said scanning to a location remote from said detector.

56. A method of filling a syringe comprising providing a drug container cradle attached to a drug container containing a drug to be administered to a patient, said drug container cradle having a flange extending therefrom supporting drug administration information, providing a scanner module having a detector for detecting said drug administration information, supporting a syringe having a needle by said scanner module, supporting said drug container cradle by said flange on said scanner module with said needle in alignment with said drug container, reading said drug administration information from said flange by said detector, inserting said needle into said drug container for loading said syringe with said drug, and storing said drug administration data.

57. The method of claim 56, further including transmitting said drug administration data to a remote location.

58. The method of claim 56, further including providing drug administration information in association with said syringe, reading said drug administration information associated with said syringe by another detector within said scanner module.

59. A drug administration system comprising a cradle attached about an injection port having a flange extending therefrom, said cradle supporting first drug information, a syringe including a needle having a flange extending from said syringe, said syringe supporting second drug administration information, and a housing slidably receiving said flange of said cradle and said syringe, whereby said needle is aligned with said injection port.

60. The system of claim 59, wherein said syringe includes a safety shield receivable within said cradle.

61. The system of claim 59, further including means within said housing for identifying said first and second drug administration information.

62. The system of claim 61, further including means for determining the amount of a drug being administered from said syringe into said injection port.

63. The system of claim 59, further including a microprocessor for storing said first and second drug administration information.

64. The cradle of claim 26, wherein said cradle and said injection port are an integral assembly.

65. The cradle of claim 26, wherein said drug administration information is provided on said flange.

66. The cradle of claim 26, wherein said injection port comprises an IV injection port.

67. A cradle adapted for attachment to an injection port, said cradle comprising a housing, a flange extending from said housing, and means for attaching said housing to said injection port, said cradle adapted for supporting thereon machine readable information.

68. The cradle of claim 67, wherein said machine readable information is provided on said flange.

69. The cradle of claim 67, wherein said injection port comprises an IV injection port.

70. The system of claim 1, further including an injection port, wherein said port cradle and said injection port are an integral assembly.

71. The system of claim 19, further including an injection port, wherein said port cradle and said injection port are an integral assembly.

72. The method of claim 30, wherein said port cradle and said injection port are an integral assembly.

73. The method of claim 40, wherein said port cradle and said injection port are an integral assembly.

74. The system of claim 59, wherein said cradle and said injection port are an integral assembly.

75. A drug administration system comprising a cradle coupled to an injection port having a flange extending therefrom, said cradle supporting first machine readable information, a syringe including a needle having a flange extending from said syringe, said syringe supporting second machine readable information, and a housing slidably receiving said flange of said cradle and said syringe, whereby said needle is aligned with said injection port.

76. The system of claim 75, further including means within said housing for reading said first and second machine readable information.

77. The system of claim 75, wherein said cradle and said injection port are an integral assembly.

78. A drug delivery system comprising a scanner module including a first and second detector; a syringe for administration of a drug, said syringe having first machine readable information provided in association therewith, said syringe constructed to be releasably attached to said scanner module in operative association with said first detector, whereby movement of said syringe relative to said first detector causes said first detector to read said first machine readable information; a port cradle coupled to an injection port, said cradle having said machine readable information provided in association therewith, said cradle constructed to be releasably attached to said scanner module in operative association with said second detector, whereby movement of said cradle relative to said second detector causes said second detector to read said second machine readable information.

79. The system of claim 78, wherein said cradle and said injection port are an integral assembly.

80. The system of claim 79, wherein said cradle comprises a holder surrounding said injection port and a flange extending therefrom.

81. The system of claim 80, wherein said scanner module includes a slotted opening for slidingly receiving said flange therein for releasably attaching said port cradle to said scanner module.

82. The system of claim 80, wherein said second machine readable information is provided on said flange.

83. A method for delivering drugs to an injection port connected to a patient, said method comprising delivering a needle on a drug loaded syringe to said injection port, automatically determining information relative to the drug contained in the syringe by electronically scanning machine readable information associated with said syringe, automatically determining information relative to the patient by electronically scanning machine readable information associated with said injection port, pushing a plunger of the syringe to deliver a quantity of the drug through the port, and storing the information obtained by scanning said machine readable information.

84. The method of claim 83, further including coupling said injection port to a port cradle having a flange to which said machine readable information is attached, said electronically scanning said machine readable information comprising moving said flange past a photosensing electronic detector.

85. The method of claim 83, wherein said injection port and said cradle comprise an integral assembly.

86. The cradle of claim 23, wherein said drug administration information is in machine readable form.

87. The method of claim 51, wherein said cradle and said injection port are an integral assembly.

* * * * *

UNITED STATES PATENT AND TRADEMARK OFFICE
CERTIFICATE OF CORRECTION

PATENT NO. : 6,685,678 B2
DATED : February 3, 2004
INVENTOR(S) : Robert F. Evans and Michael F. Burrow It is certified that error appears in the above-identified patent and that said Letters Patent is hereby corrected as shown below:

Column 20,
Line 33, "inection" should read -- injection --.

Signed and Sealed this

Eleventh Day of May, 2004

JON W. DUDAS
*Acting Director of the United States Patent and Trademark Office*